US012691093B2

(12) United States Patent
Lu et al.

(10) Patent No.: US 12,691,093 B2
(45) Date of Patent: Jul. 28, 2026

(54) METHODS TO SENSITIZE CANCER CELLS TO IMMUNE ATTACK USING ATRACTYLENOLIDE I

(71) Applicant: THE TRUSTEES OF INDIANA UNIVERSITY, Bloomington, IN (US)

(72) Inventors: Xiongbin Lu, Carmel, IN (US); Xinna Zhang, Carmel, IN (US); Kevin Van Der Jeught, Indianapolis, IN (US)

(73) Assignee: THE TRUSTEES OF INDIANA UNIVERSITY, Bloomington, IN (US)

( * ) Notice: Subject to any disclaimer, the term of this patent is extended or adjusted under 35 U.S.C. 154(b) by 511 days.

(21) Appl. No.: 18/035,694

(22) PCT Filed: Nov. 30, 2021

(86) PCT No.: PCT/US2021/061295

§ 371 (c)(1),
(2) Date: May 5, 2023

(87) PCT Pub. No.: WO2022/125339

PCT Pub. Date: Jun. 16, 2022

(65) Prior Publication Data

US 2023/0404967 A1 Dec. 21, 2023

Related U.S. Application Data

(60) Provisional application No. 63/122,232, filed on Dec. 7, 2020.

(51) Int. Cl.

| | |
|---|---|
| ***A61K 31/365*** | (2006.01) |
| ***A61K 40/11*** | (2025.01) |
| ***A61K 40/32*** | (2025.01) |
| ***A61K 40/42*** | (2025.01) |
| ***A61K 45/06*** | (2006.01) |
| ***A61P 35/00*** | (2006.01) |
| ***C12N 5/0783*** | (2010.01) |

(52) U.S. Cl.

CPC ............ *A61K 31/365* (2013.01); *A61K 40/11* (2025.01); *A61K 40/32* (2025.01); *A61K 40/42* (2025.01); *A61K 45/06* (2013.01); *A61P 35/00* (2018.01); *C12N 5/0638* (2013.01)

(58) Field of Classification Search

None

See application file for complete search history.

(56) References Cited

U.S. PATENT DOCUMENTS

| | | | | |
|---|---|---|---|---|
| 2015/0147314 | A1* | 5/2015 | Jefferies ............... | A61K 31/045 435/375 |
| 2017/0202937 | A1 | 7/2017 | Weinschenk et al. | |
| 2019/0321370 | A1 | 10/2019 | Sorrentino et al. | |

FOREIGN PATENT DOCUMENTS

| | | | |
|---|---|---|---|
| CN | 108478557 | A | 9/2018 |
| CN | 111686075 | A | 9/2020 |
| WO | 1997034472 | A1 | 9/1997 |

OTHER PUBLICATIONS

Takeda, K. et al. Components of the root of Lindera Strychnifolia VILL.-XI. Tetrahedron 1966, 22, 1159-1167. (Year: 1966).*

Wang, K. et al. Atractylenolide I inhibits colorectal cancer cell proliferation by affecting metabolism and stemness via AKT/mTOR signaling. Phytomedicine 2020, 68, 153191; Available online: Feb. 14, 2020. (Year: 2020).*

Extended EP Search Report mailed Sep. 24, 2019 and issued in connection with EP Appln. No. 21904128.2, 18 pages.

Bailly, Christian, "Atractylenolides, essential components of Atractylodes-based traditional herbal medicines: Antioxidant, anti-inflammatory and anticancer properties", European Journal of Pharmacology, Elsevier Science, NL, vol. 891, Nov. 18, 2020 (Nov. 18, 2020), 15 pages.

Zhang, Dongyong, et al., "Temozolomide increases MHC-I expression via NF-[kappa]B signaling in glioma stem cells", Cell Biology International, Academic Press, GB, vol. 41, No. 6, May 2, 2017 (May 2, 2017), 11 pages.

PCT International Search Report and Written Opinion completed by the ISA/US on Jan. 30, 2022 and issued in connection with PCT/US2021/061295.

Liu et al., "Atractylenolide I modulates ovarian cancer cell-mediated immunosuppression by blocking MD-2/TLR4 complex-mediated MyD88/NF-κB signaling in vitro", (2016), J Transl Med (2016) 14:104 DOI 10.1186/s12967-016-0845-5; entire document, especially abstract, p. 3 col. 1 para 2, p. 6 col. 1 para 2, p. 6 col. 2 para 1, p. 10 col. 1 para 1.

Chan et al., "Anti-Tumor Activity of Atractylenolide I in Human Colon Adenocarcinoma In Vitro," Molecules, Jan. 4, 2020, pp. 1-14.

Chinese Office Action for Application No. CN202180082055, dated Jul. 10, 2025.

Liu et al., "Atractylenolide I modulates ovarian cancer cell-mediated immunosuppression by blocking MD-2/TLR4 complex-mediated MyD88/NF-κB signaling in vitro," J Transl Med (2016) 14:104, URL: https://pmc.ncbi.nlm.nih.gov/articles/PMC4847224/.

(Continued)

*Primary Examiner* — Jeffrey H Murray

*Assistant Examiner* — Kristen W Romero

(74) *Attorney, Agent, or Firm* — Barnes & Thornburg LLP

(57) ABSTRACT

The present disclosure relates to compositions and methods to induce or increase immunogenicity in cancerous cells comprising contacting the cancerous cells with atractylenolide I (ATT-I). In some embodiments, the methods include contacting the cancerous cells with ATT-I in combination with a cancer therapeutic agent.

2 Claims, 18 Drawing Sheets

Specification includes a Sequence Listing.

(56) References Cited

OTHER PUBLICATIONS

Li et al., "Atractylenolide I Induces Apoptosis and Suppresses Glycolysis by Blocking the JAK2/STAT3 Signaling Pathway in Colorectal Cancer Cells," Front. Pharmacol. (2020) 11:273, URL: https://pmc.ncbi.nlm.nih.gov/articles/PMC7114890/.

Japanese Office Action for patent application No. 2023-534277, dated Aug. 15, 2025 (English Translation).

* cited by examiner

METHODS TO SENSITIZE CANCER CELLS TO IMMUNE ATTACK USING ATRACTYLENOLIDE I

CROSS REFERENCE TO RELATED APPLICATIONS

This application us a U.S national counterpart application of international application serial No. PCT/US2021/061295 filed Nov. 30, 2021, which claims priority to U.S. Provisional Patent Application No. 63/122,232 filed on Dec. 7, 2020, the disclosures of which are hereby expressly incorporated herein by reference in their entireties.

INCORPORATION BY REFERENCES OF MATERIAL SUBMITTED ELECTRONICALLY

Incorporated by reference in its entirety is a computer-readable nucleotide/amino acid sequence listing submitted concurrently herewith and identified as follows: 1 kilobytes ACII (Text) file named "348382_ST25.txt," created on Oct. 28, 2021.

BACKGROUND

The immune system can distinguish healthy cells from tumor cells, as the latter expresses tumor associated antigens (TAAs). In the context of CD8+ T cell-mediated immune responses, recognition of TAAs occurs through the presentation of TAAs via MHC-I on tumor cells and their interaction with T cell receptor (TCR) on the CD8+ T cells. Impairing this event will ultimately reduce or annihilate the CD8+T cell-mediated tumor cytotoxicity. However, reduction or loss of antigen presentation is a frequent and essential mechanism used by tumor cells to escape immune recognition and destruction. Conversely, increasing the presentation of antigen-loaded MHC-I complex on cancer cells renders them sensitive to T cell-mediated killing.

The present disclosure relates generally to a method of increasing immunogenicity in a cancer cell. More specifically, the disclosure relates to a method of contacting a cancer cell with atractylenolide I to prompt the cancer cell's production of MHC-I, resulting in the ability of an immune cell to recognize and attack the cancer cell.

SUMMARY

While great advancements have been made in cancer immunotherapy technology, the cancer's ability to disguise itself and evade detection is still an issue. Described herein are methods to activate antigen processing and presentation on a cancer cell making it readily identifiable to an immune cell. More particularly, the present disclosure provides methods comprising contacting a cancer cell with atractylenolide I (referred to as ATT-I) to enhance the ability of an immune cell to recognize and attack the cancer cell.

The binding of small molecule ATT-I to a cancer cell's proteasome 26S subunit non-ATPase 4 (PSMD4) augments the antigen processing activity of the cell's immunoproteasome complex and enhances the major histocompatibility class I (MHC-I)-mediated antigen presentation on the cancer cell. In essence, by contacting a cancer cell with ATT-I, the cancer cell begins to express antigens on its surface allowing an immune cell to recognize and attack it. Specifically, the present disclosure describes enhancing CD8+ T-cell's ability to recognize a cancer cell after exposure of the cancer cell to ATT-I.

In some aspects, the disclosure provides methods of using ATT-I in combination with another therapeutic molecule to increase tumor infiltration and sensitivity to CD8+ T-cell cytotoxicity. In one embodiment, a method of contacting a cancer cell with ATT-I is provided, wherein the ATT-I increases the cancer cell's sensitivity to CD8+ T-cell cytotoxicity. In some aspects, ATT-I is substantially pure, is about 98% pure, about 97% pure, about 96%, about 95% pure, or about 90% pure.

In one embodiment a method of enhancing the efficacy of CD8+ T cell cytotoxicity against a cancerous cell is provided wherein the method comprises contacting said cancerous cell with atractylenolide (ATT-I). In accordance with one embodiment the cancerous cell is contacted in vivo by administration of a pharmaceutical composition comprising ATT-1. In one embodiment the method of enhancing the efficacy of CD8+ T cell cytotoxicity comprises administering a pharmaceutical composition comprising ATT-1 to a patient diagnosed with cancer, optionally in conjunction with the administration of a checkpoint inhibitor and optionally in conjunction with administration of an anti-cancer immunotherapeutic agent. In one embodiment the checkpoint inhibitor is an inhibitor of cytotoxic T-lymphocyte associated protein 4 (CTLA-4) or programmed death ligand 1 (PD-L1) and the cancerous cell is a colorectal cancer (CRC) cell.

In one embodiment a method of increasing the presentation of antigen-loaded MHC-I complex on a cancer cell is provided, wherein the method comprises contacting said cancer cell with ATT-I, optionally wherein the cancer cell is a colorectal cancer (CRC) cell.

In one embodiment, a method of treating a tumor is provided wherein the cells of the tumor are contacted with ATT-I in combination with one or more additional therapeutic molecule, including for example, administration of one or more checkpoint inhibitors. In some embodiments, the therapeutic molecule comprises a programmed death-1 (PD-1) inhibitor, optionally wherein the inhibitor is selected from atezolizumab, durvalumab and avelumab. In some embodiments, the therapeutic molecule comprises an inhibitor of cytotoxic T-lymphocyte associated protein 4 (CTLA-4) or programmed death ligand 1 (PD-L1). In some embodiments, a method of treating a tumor with ATT-I in combination with a CTLA-4 and/or PD-L1 inhibitor is provided. In one embodiment, a method of treating cancer is provided, wherein the method comprises administering a pharmaceutical composition comprising atractylenolide (ATT-I) to a patient diagnosed with cancer. In one embodiment the cancer to be treated is a solid tumor, optionally wherein the cancer is colorectal cancer (CRC). In accordance with one embodiment the pharmaceutical composition comprising atractylenolide (ATT-I) is administered to a patient diagnosed with cancer that is receiving anti-cancer immunotherapy. In a further embodiment the patient receiving ATT-I can be further administered a checkpoint inhibitor either simultaneously or before or after administration of ATT-I, optionally wherein the checkpoint inhibitor is an inhibitor of cytotoxic T-lymphocyte associated protein 4 (CTLA-4) or programmed death ligand 1 (PD-L1).

In one embodiment a method of sensitizing a cancer cell to attack from an immune cell is provided, wherein the method comprising contacting the cancer cell with ATT-I. In one embodiment the immune cell is engineered or native, and in one embodiment the immune cell is a CD8+ T-cell.

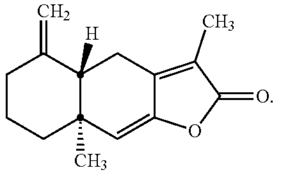

Figure 1A:
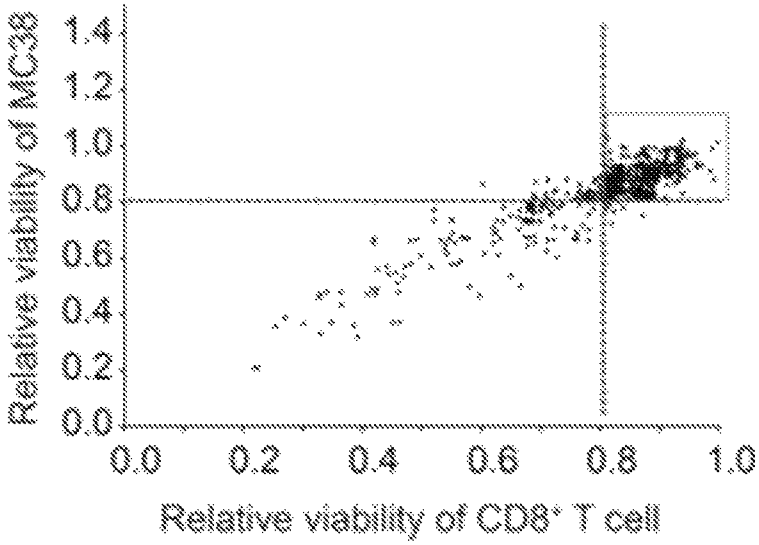
FIGS. 1A-IF present data showing ATT-I enhances the killing efficiency of CD8+ T cells against tumor cells. A total of 594 natural small molecule compounds purified from traditional medicinal plants were tested for their toxicity on MC38 cells and T cells freshly isolated from C57BL/6 mice. Data are presented as mean of 3 independent experiments (FIG. 1A).
Figure 1B:
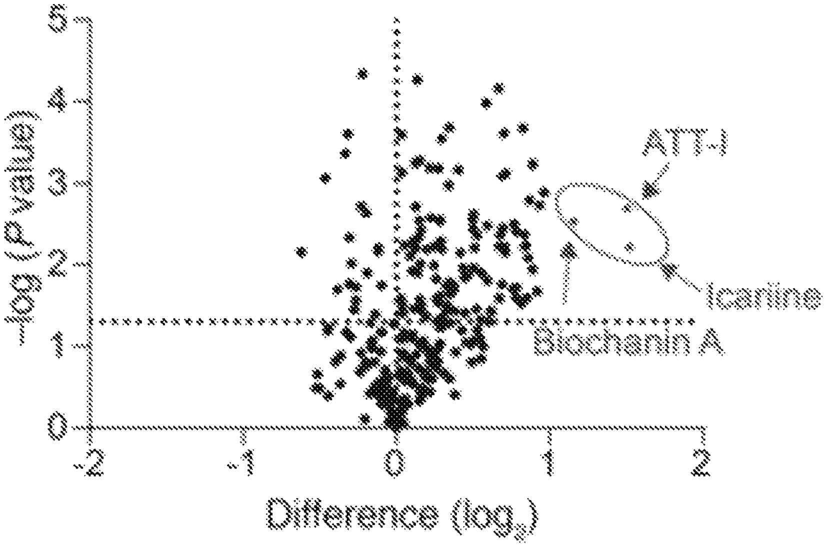
FIG. 1B shows the result of 446 drugs with low toxicity from tested for their effects on the CD8+ T cell-mediated cytotoxicity. MC38-OVA cells expressing luciferase were co-cultured with OT-I CD8+ T cells in the presence of each drug (5.0 μM) and the T cell-mediated cytotoxicity was measured by the luciferase assay. Difference (log 2): (log 2 [relative viability] >1; P<0.05). Relative viability=(tumor cell viability of treated group)/(tumor cell viability of control group). Data are presented as mean of 3 independent experiments. Statistical analysis was conducted using 1-way ANOVA. The chemical structure of ATT-I is as follows.
Figure 1C:
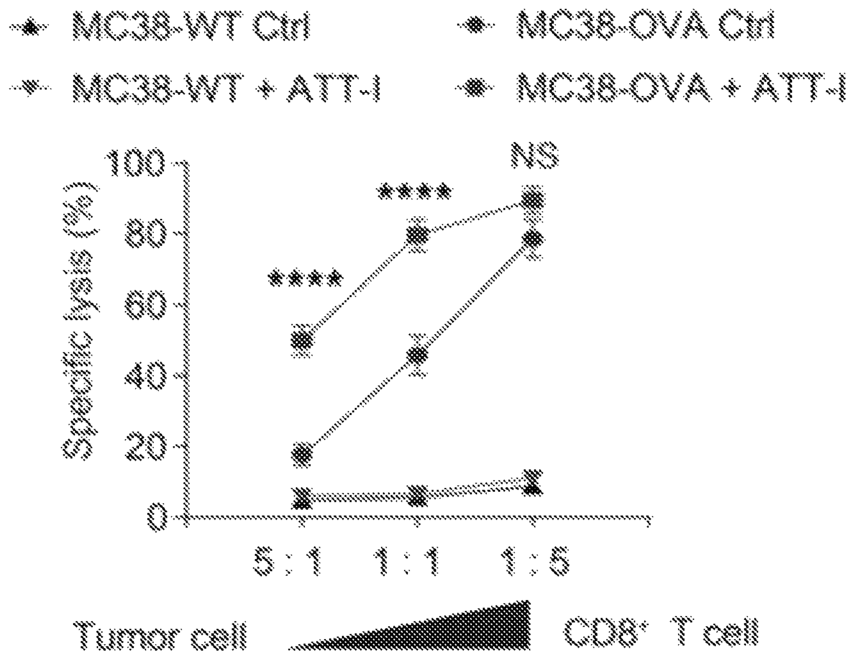
Figure 1D:
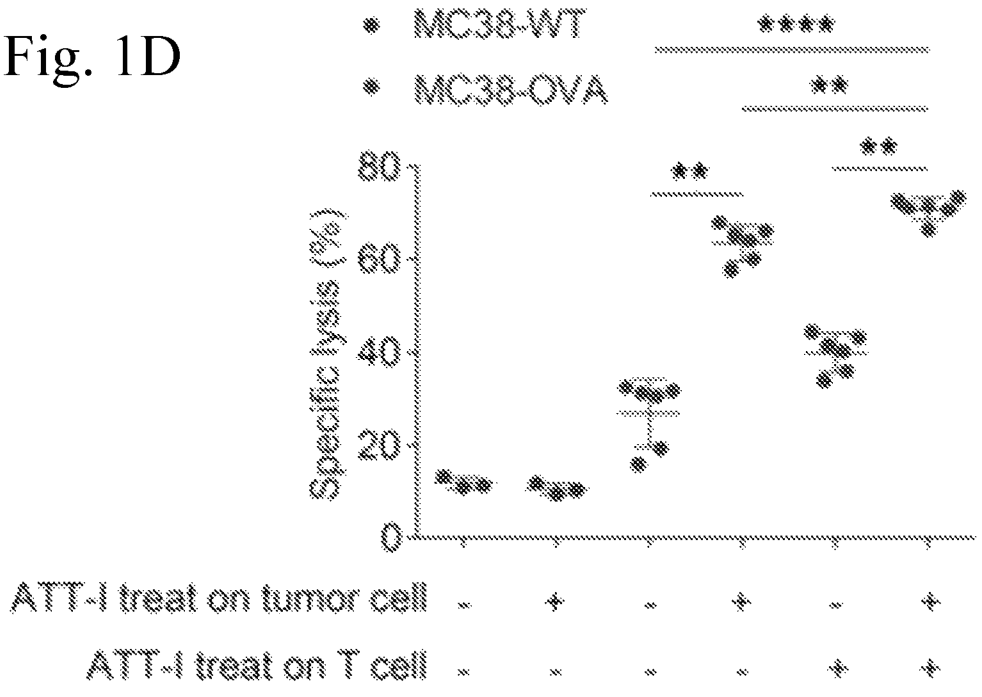

The effect of ATT-I treatment on the CD8+ T cell killing of MC38-OVA cells was measured under different ratios of tumor cells versus T cells and the results are shown in FIG. 1C. Data are presented as mean±SD of 3 independent experiments. Statistical analysis was conducted using 2-way ANOVA. FIG. 1D presents data from CD8+ T cell killing assays conducted using co-culture of OT-I CD8+ T cells with MC38-WT cells (lanes 1 and 2) or MC38-OVA cells (lanes 3-6) pretreated with 5 μM of ATT-I (+) or vehicle control DMSO (−). Data are presented as mean±SD of 3 independent experiments. The levels of IFN-γ (FIG. 1E) and TNF-α (FIG. 1F) in the supernatants after co-culture of OT-I T cells with MC38-WT cells (lanes 1 and 2) or MC38-OVA cells (lanes 3-6) pretreated with ATT-I (+) or DMSO control (−) were determined by ELISA. Data are presented as mean±SD of 3 independent experiments. Statistical analyses were conducted using 2-way ANOVA.  P<0.01; * P<0.001; **** P<0.0001.

Figure 2:
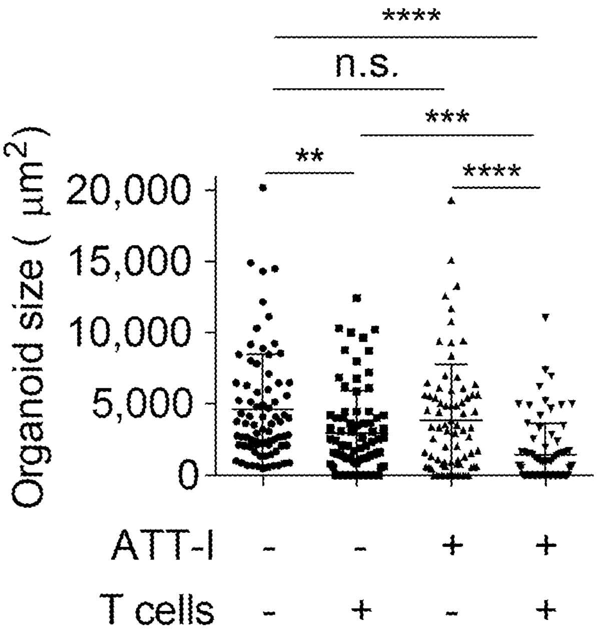

FIG. 2: ATT-I enhances the antigen-specific T cell responses in MC38 tumor-derived organoids. OT-I CD8+ T cells were co-cultured with tumor organoids generated from MC38-derived tumors in C57BL/6 mice with or without ATT-I treatment. FIG. 2 is a graph representing the quantification of the organoid size presented as mean±SD of 3 parallel experiments. The size of organoids was measured as project area (μm2) using Image J software. Statistical analysis was conducted using 2-way ANOVA.  P<0.01; * P<0.001; **** P<0.0001.

Figure 3A:
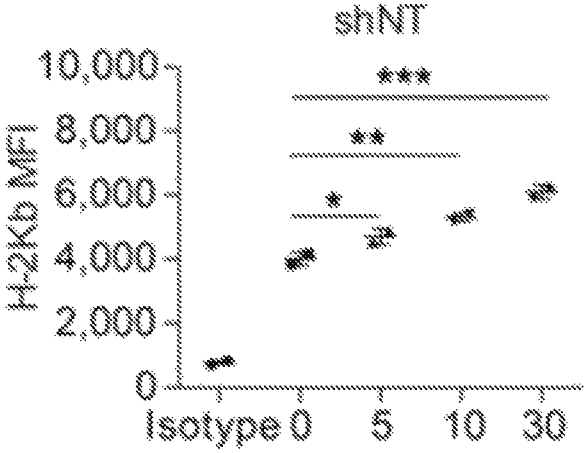
Figure 3B:
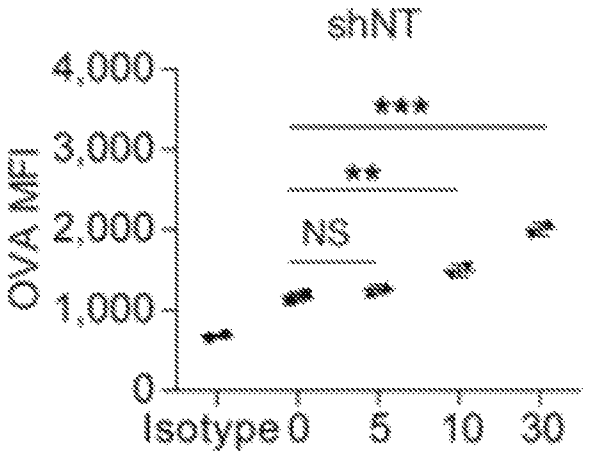
Figure 3C:
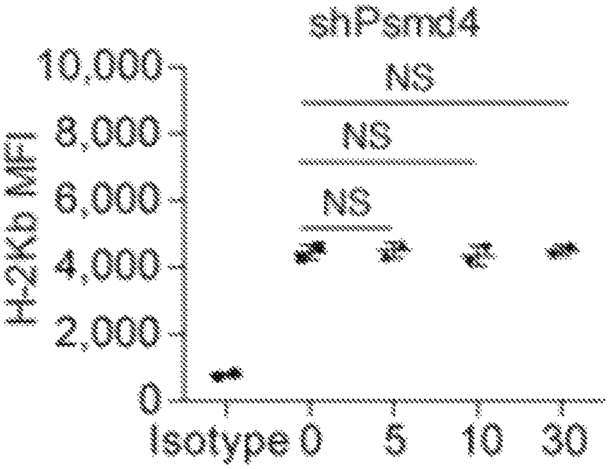
Figure 3D:
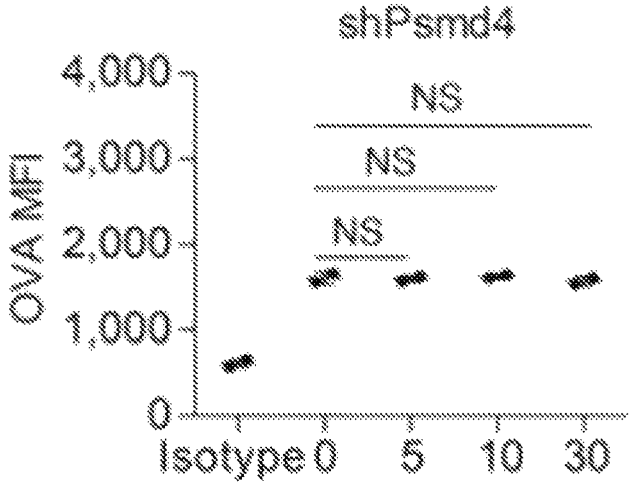
Figure 3E:
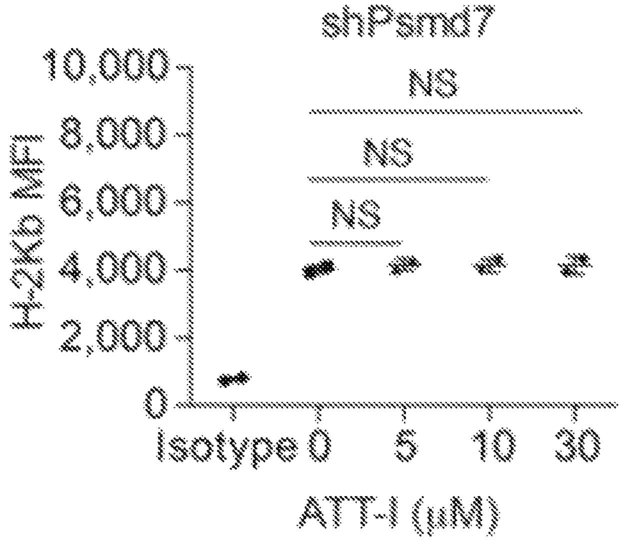
Figure 3F:
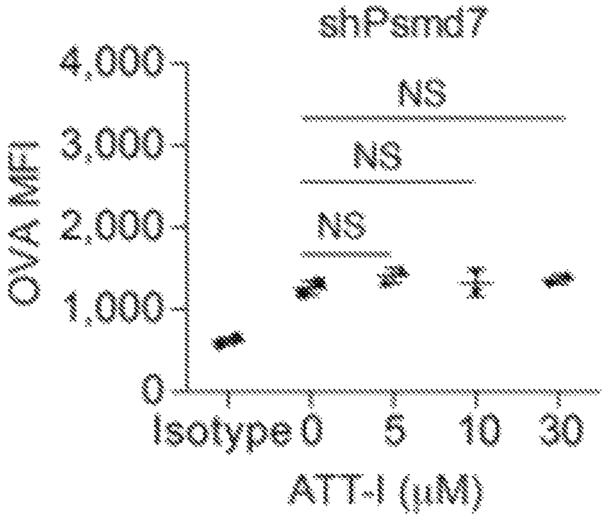
Figure 3G:
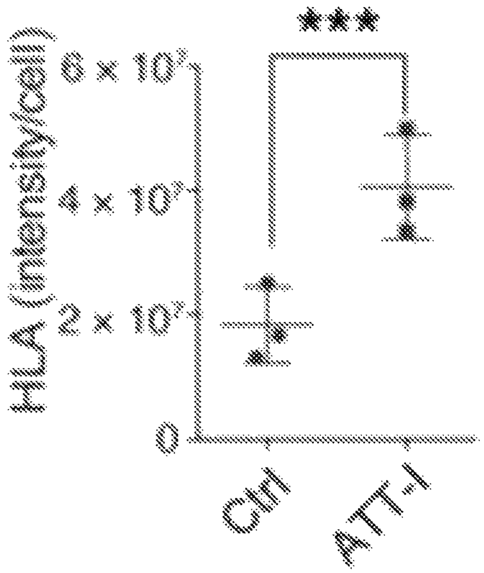
Figure 3H:
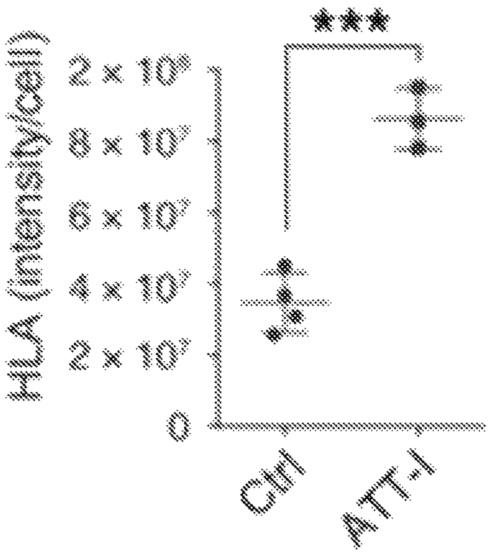
Figure 3I:
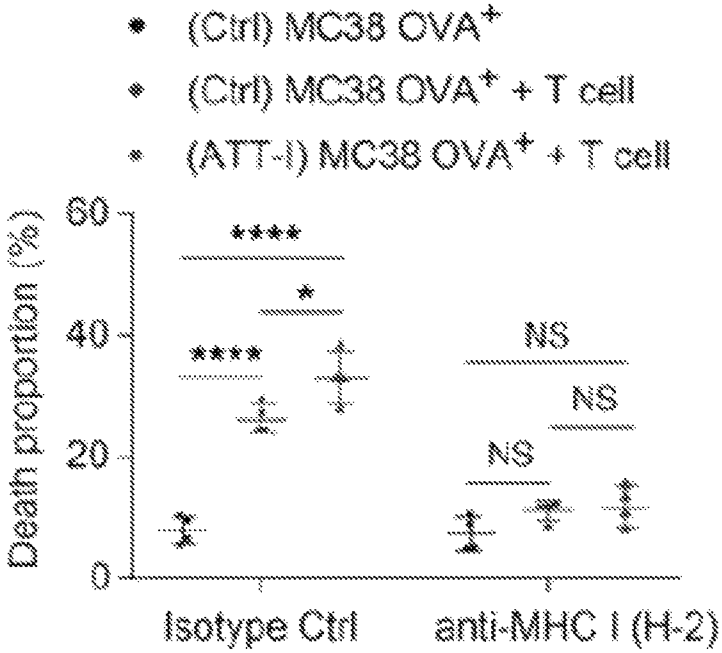

FIG. 3A-3I: ATT-I enhances antigen presentation on tumor cells. FIGS. 3A-3F are graphs showing MFI values of H-2Kb and H-2Kb-SIINFEKL (OVA) on the MC38-OVA cells (shNT control (FIGS. 3A & 3B), shPsmd4 (FIGS. 3C & 3D), and shPsmd7 (FIGS. 3E & 3F)) treated with ATT-I (0, 5, 10, and 30 μM), which were determined by flow cytometry analysis. Data are presented as mean±SEM and are representative of 2 independent experiments (n=2). Statistical analysis was conducted using 1-way ANOVA. HLA-A,B,C on the surface of HCT116 cells and SW837 cells was analyzed by 3D confocal imaging of immunofluorescence. Cell nucleus was stained by 4',6-diamidino-2-phenylindole (DAPI). Quantitative data are presented (in FIG. 3G for HCT116 cells and in FIG. 3H for SW837 cells) as mean±SD of 3 to 4 parallel experiments (n=3-4). Unpaired 2-tailed t test was used for statistical analysis. FIG. 3I presents data demonstrating the effect of ATT-I on the cytotoxicity of MC38 OVA+after blocking the MHC-I/TCR interaction using the MHC-I antibody (lanes 1 and 4: vehicle control-treated MC38 OVA+ cells; lanes 2 and 5: vehicle control-treated MC38 OVA+ cells plus T cells; lanes 3 and 6: ATT-I-treated MC38 OVA+ cells plus T cells). Specifically, we treated MC38 OVA+ cells with and without 30 μM ATT-I for 48 hours. Rat IgG2a isotype control and anti-mouse MHC class I (H2) were used for blocking the cells overnight. The antigen-specific cytotoxicity was analyzed by flow cytometry. Data are presented as mean #SEM and are representative of 2 independent experiments (n=4). Statistical analysis was conducted using 1-way ANOVA. * P<0.05;  P<0.01; * P<0.001.

Figure 4A:
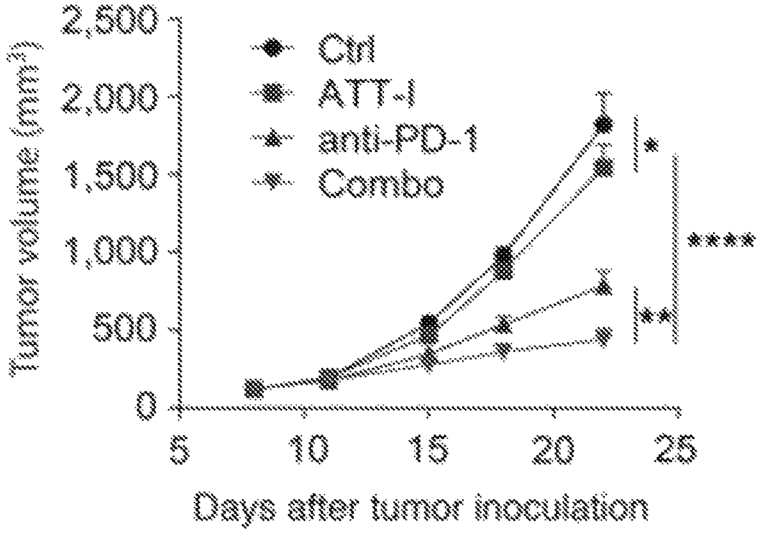
Figure 4B:
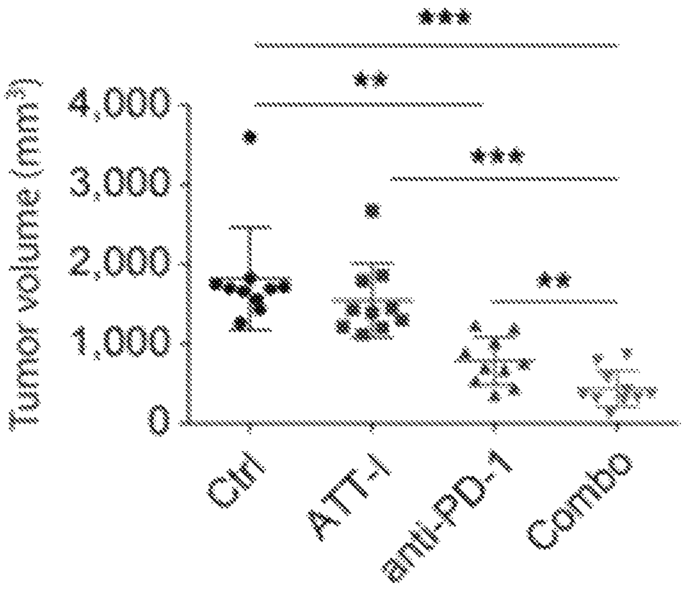
Figure 4C:
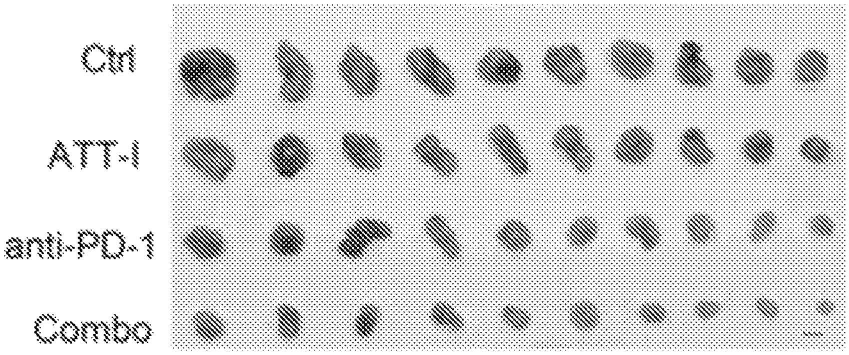
Figure 4D:
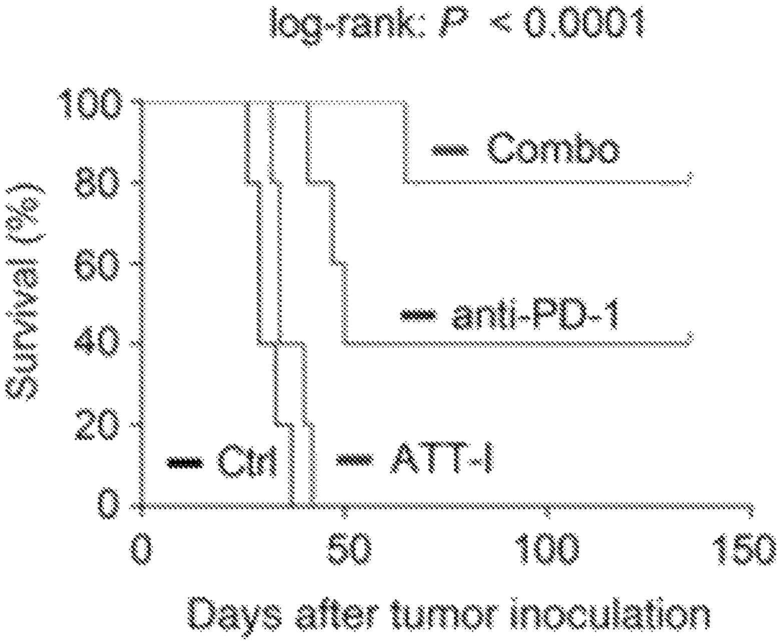
Figure 4E:
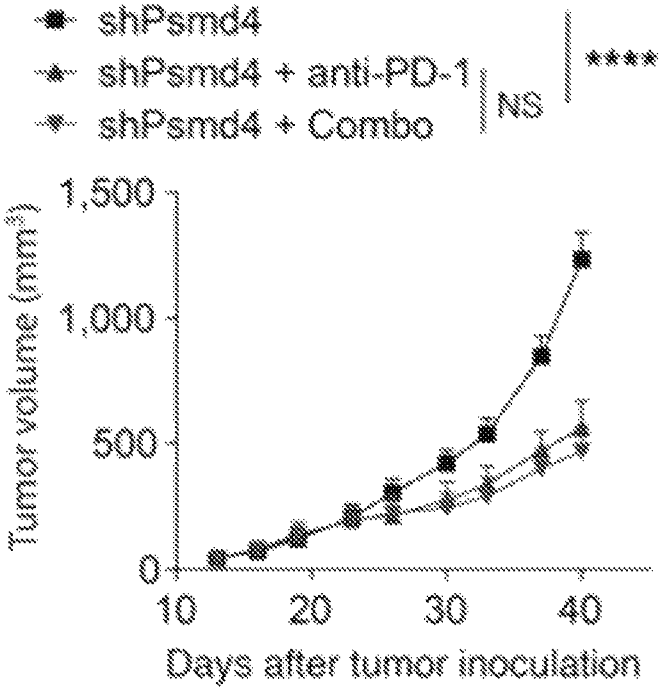

FIG. 4A-4E: ATT-I enhances the immune checkpoint blockade immune responses. FIGS. 4A-4C demonstrate the effects of the ATT-I (daily) and anti-PD-1 (3 times/week, 5 injections in total) on tumor growth (FIG. 4A) and tumor volume (FIG. 4B) of MC38-derived tumors in the subcutaneous C57BL/6 mouse model. Error bars represent SEM (n=10 mice per group). Data shown are representative of 2 independent experiments. Statistical analysis was conducted using 2-way ANOVA (FIG. 4A) and 1-way ANOVA (FIG. 4B). Pictures of the resected tumors are shown in FIG. 4C. Scale bar: 1 cm. The effects of the ATT-I (50 mg/kg, daily) and anti-PD-1 (200 μg/mouse, 3 times/week, 5 injections in total) on tumor growth, measured via bioluminescence imaging, and survival on the orthotopic MC38-derived tumor model (log-rank test), and survival rates are shown in FIG. 4D. Each group includes 5 mice. Graphs presenting tumor growth curves of MC38-derived tumors with or without PSMD4 knockdown and treated with anti-PD-1 only or anti-PD-1 together with ATT-I (combo) are shown in FIG. 4E. Each group includes 6 mice. Statistical analysis was conducted using 2-way ANOVA. * P<0.05;  P<0.01; * P<0.001; **** P<0.0001.

Figure 5A:
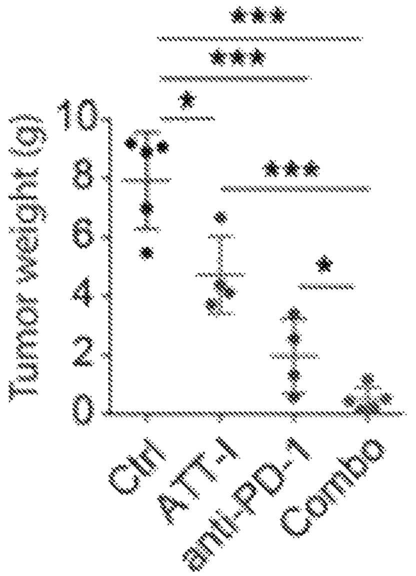
Figure 5B:
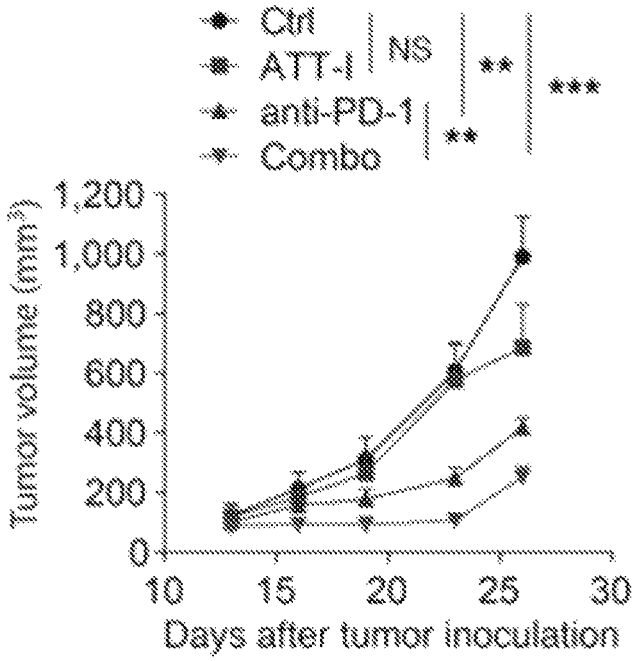
Figure 5C:
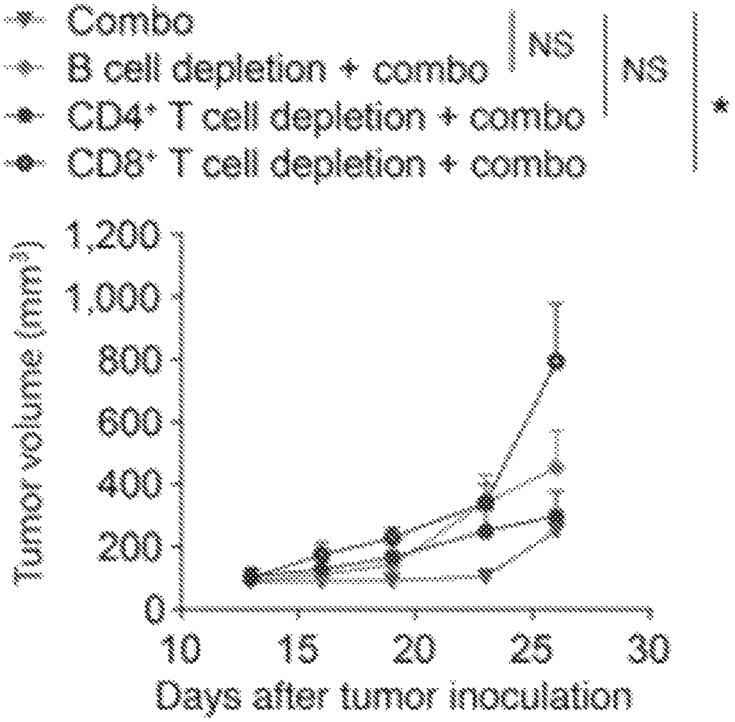
Figure 5D:
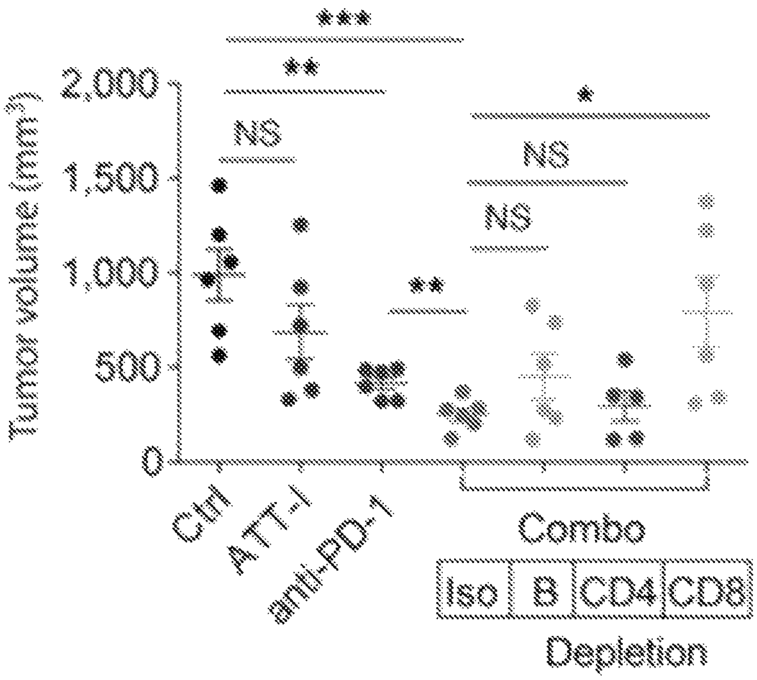

FIG. 5A-5D: ATT-I enhances tumor-infiltrating lymphocytes and antitumor activity of cytotoxic T lymphocytes. Mice received orthotopic cecal wall implantation of MC38 cells and were treated with ATT-1, PD-1 antibodies, or a combination and the tumors were resected after 28 days for the analysis of tumor microenvironment using mass cytometry (CyTOF). Orthotopic MC38 tumors were surgically resected 28 days after implantation, dissociated to single cells, and stained with metal isotope-conjugated antibodies. Immune profiles were assessed via CyTOF (26 markers) and analyzed using the Cytobank platform. viSNE analysis was performed, and thereafter SPADE on viSNE was assessed for an overlaid clustering of the immune cell populations. FIG. 5A is a graph presenting representative MC38 weights of cecal wall implanted tumors (n=5 in each group). Statistical analysis was conducted using 1-way ANOVA. Percentages of distinct immune cell populations within the CD45+ infiltrating immune cells in colorectal cancer tumors analyzed with Cytobank (n=5) are presented in Table 1. Once the subcutaneous MC38 tumors were established, mice were randomly assigned into 7 groups and treated as indicated in FIGS. 5B-5D. Effects of the ATT-I (50 mg/kg, daily) and anti-PD-1 (3 times/week, 5 injections in total) treatment on tumor growth (FIG. 5B and FIG. 5C) and tumor volume (FIG. 5D) upon depletion of B cells, CD4+ T cells, and CD8+ T cells (n=6). Iso indicates isotype control antibody. Error bars represent SEM and statistical analysis were conducted using 2-way ANOVA (E and F) and 1-way ANOVA (G). * P<0.05;  P<0.01; * P<0.001.

Figure 6A:
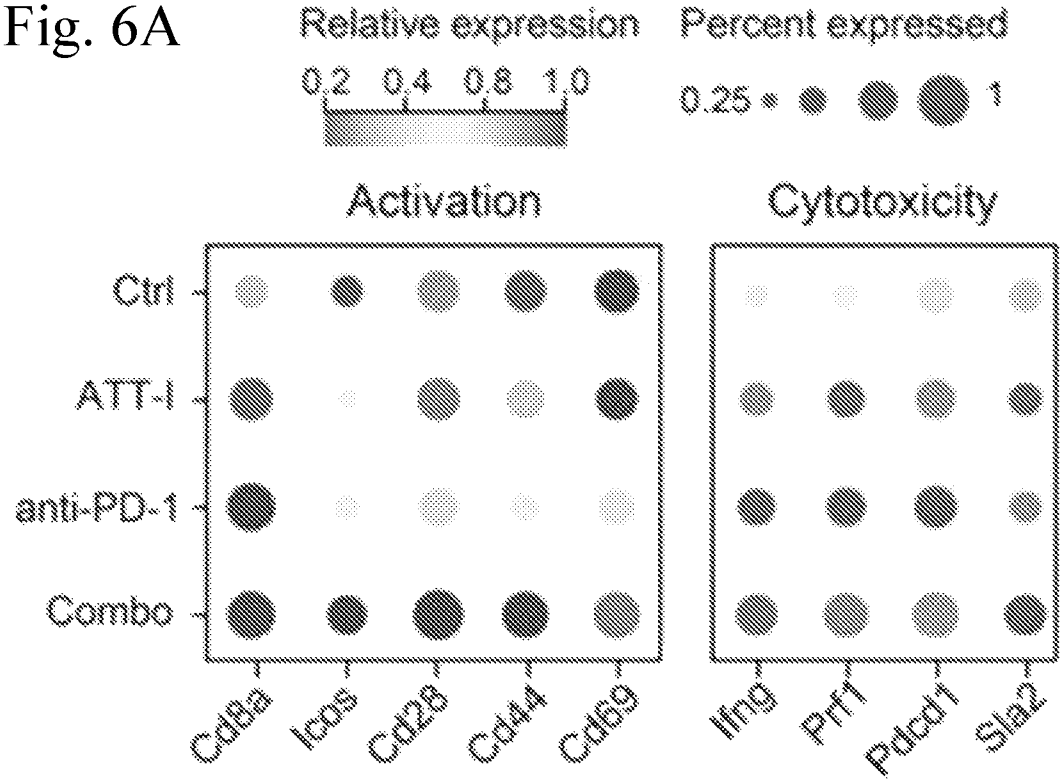
Figure 6B:
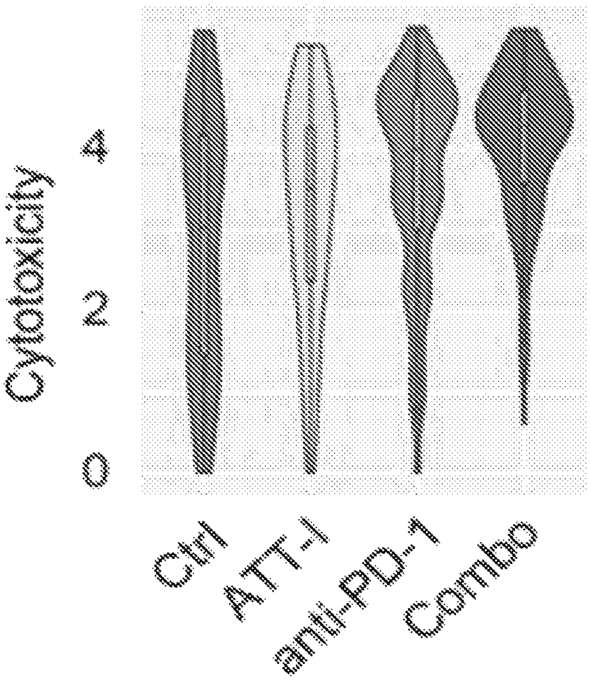
Figure 7A:
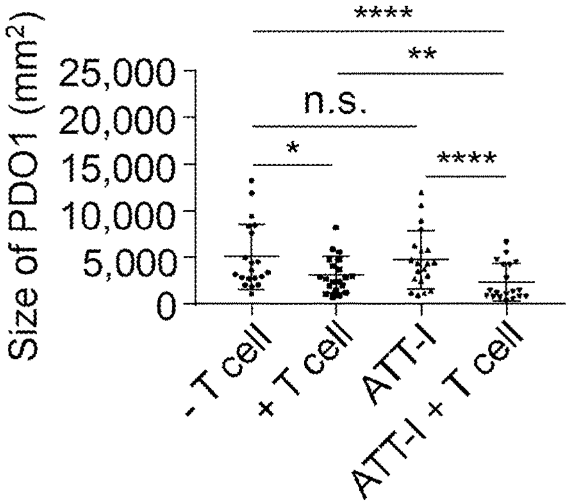
Figure 7B:
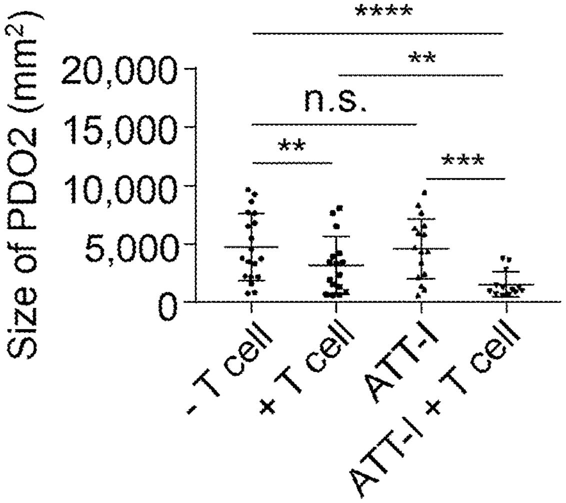
Figure 7C:
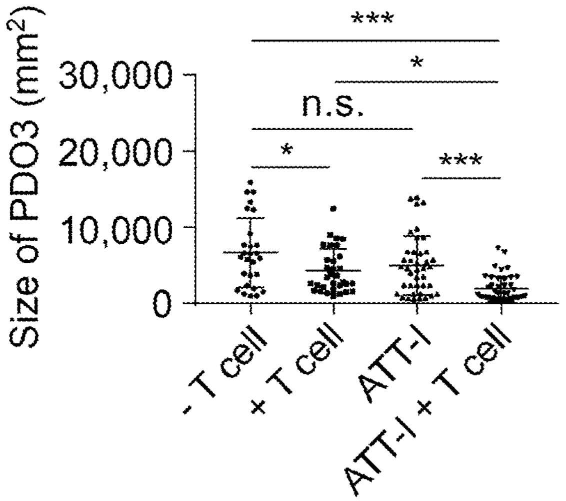
Figure 7D:
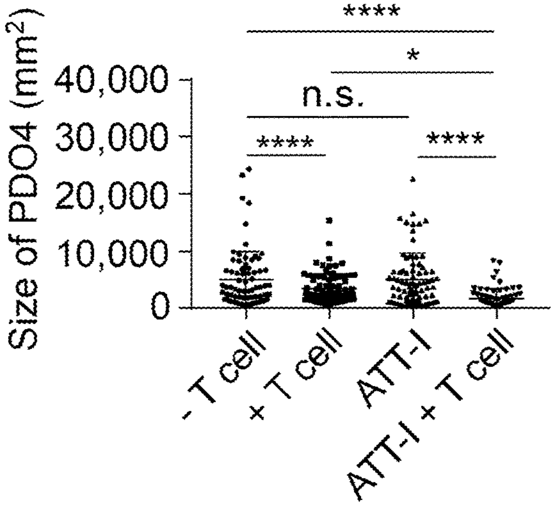
Figure 7E:
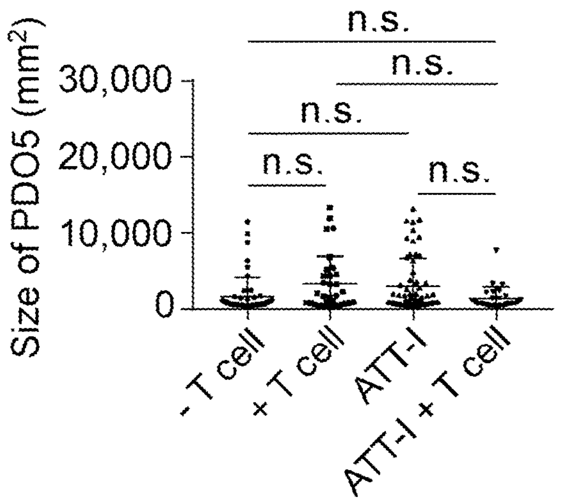
Figure 7F:
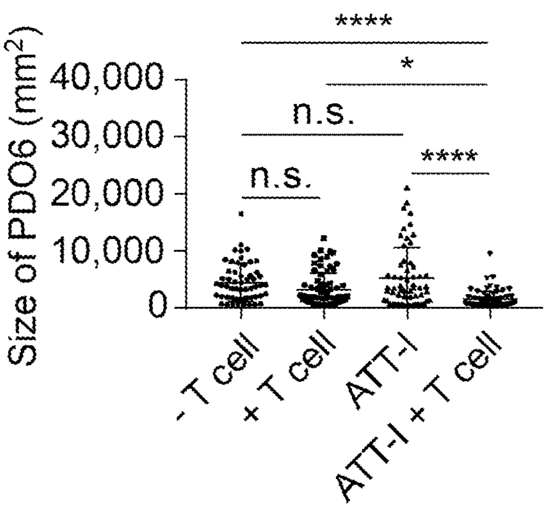
Figure 7G:
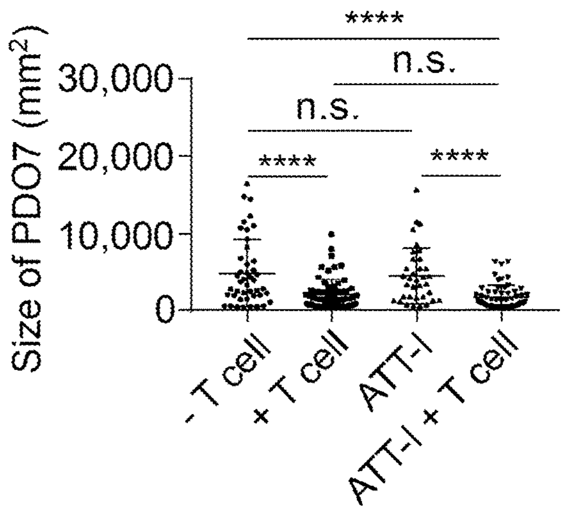
Figure 7H:
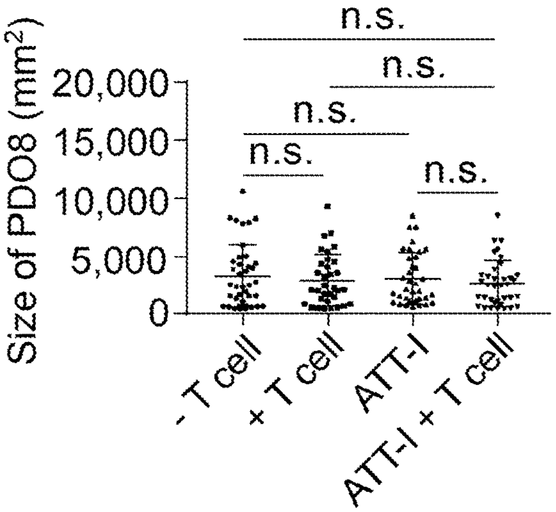

FIG. 6A-6B: Single-cell RNA-seq analysis of mouse colorectal tumors treated with ATT-I in combination with immune checkpoint blockade therapy. C57BL/6 mice bearing orthotopic implanted MC38-derived tumors were treated with vehicle control, ATT-I (50 mg/kg, daily), anti-PD-1 (3 times/week, 5 times in total), or ATT-I+anti-PD-1 combo. Tumors were harvested 2 weeks after initial treatment (5 tumor samples were pooled per arm). Cell types were assessed by the expression levels of known marker genes abd gene expression profiles of functional marker genes in selected immune cell types were analyzed. Averaged expression levels of T cell activation and cytotoxic marker genes in the CD8+ effector T cells from different conditions is shown in FIG. 6A. The dot size characterizes the proportion of CD8+ effector T cells of each condition (y axis) with expression levels (indicated by intensity) of the selected genes (x axis). FIG. 6B provides the distribution of cytotoxicity scores of CD8+ effector T cells under each condition. Cytotoxic level of each cell is inferred by the averaged expression level of CD8+T marker genes Prf1, Ifng, Tnf, Pdcd1, Sla2, and Cd8a. The y axis represents the cytotoxicity score. Combo versus anti-PD-1 (P=1.121× 10-6); combo versus ATT-1 (P=0.0024). Statistical analysis was conducted using unpaired 2-tailed t test.

FIGS. 7A-7H: ATT-I enhances the autologous T cell responses in CRC patient-derived tumor organoids. Patient-derived organoids (PDOs) were co-cultured with autologous CD8+ T cells in the presence or absence of ATT-I. Quantification of the organoid size presented as mean±SD from 8 different patients (PDO1-PDO8; shown in FIGS. 7A-7H). The size of organoids was measured as project area (μm2) using Image J software. Statistical analysis was conducted using 1-way ANOVA.

Figure 8A:
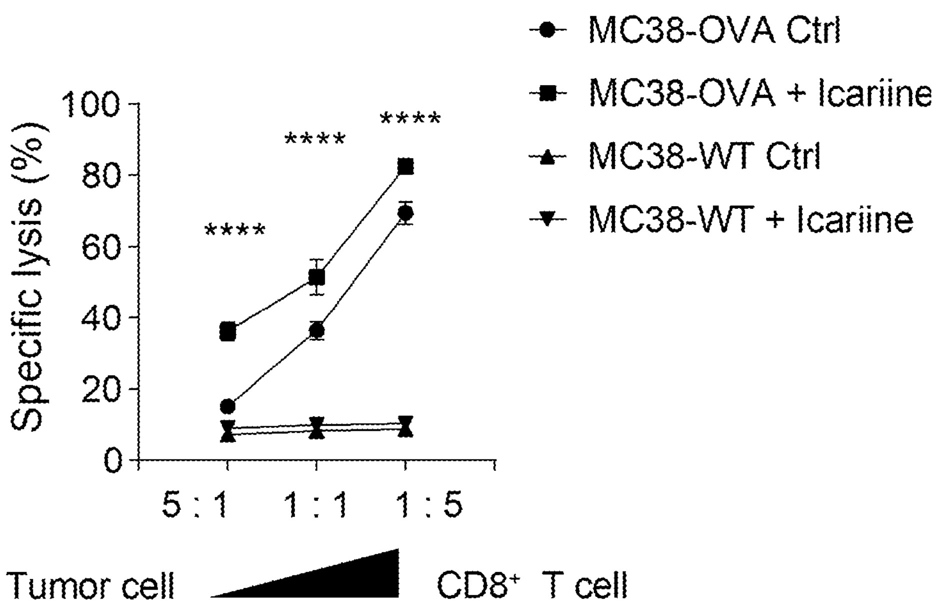
Figure 8B:
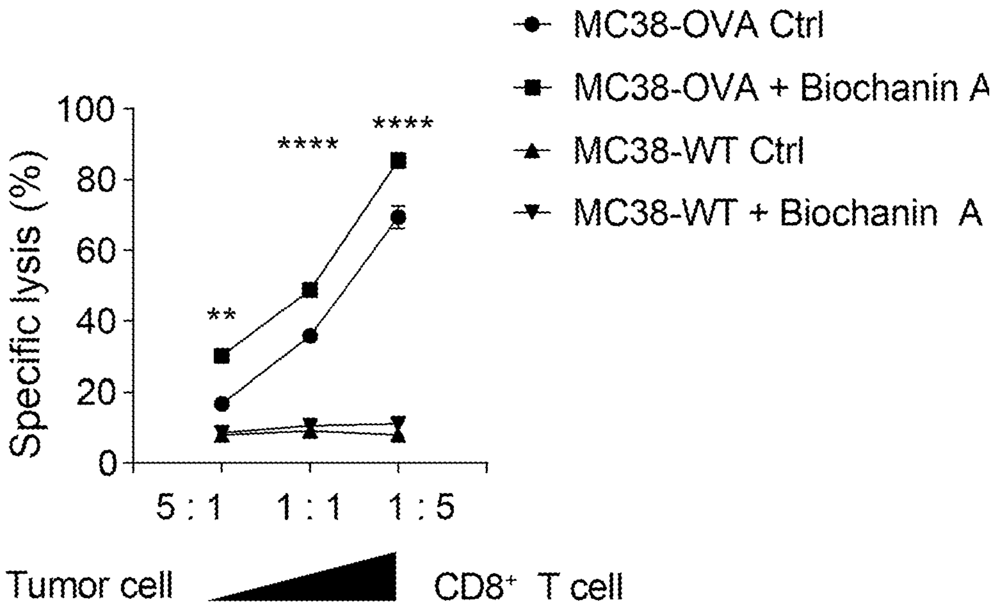

FIGS. 8A and 8B show the effect of Icariine or Biochanin A treatment on the CD8+ T-cell killing of MC38-OVA cells was measured under different ratios of tumor cells vs T cells as indicated. Data are presented as mean±SD of three independent experiments. Statistical analyses were conducted using two-way ANOVA test.

DETAILED DESCRIPTION

Definitions

In describing and claiming the invention, the following terminology will be used in accordance with the definitions set forth below.

The term "about" as used herein means greater or lesser than the value or range of values stated by 10 percent but is not intended to limit any value or range of values to only this broader definition. Each value or range of values preceded by the term "about" is also intended to encompass the embodiment of the stated absolute value or range of values.

As used herein, the term "purified" and like terms relate to the isolation of a molecule or compound in a form that is substantially free of contaminants normally associated with the molecule or compound in a native or natural environment. As used herein, the term "purified" does not require absolute purity; rather, it is intended as a relative definition.

The term "isolated" requires that the referenced material be removed from its original environment (e.g., the natural environment if it is naturally occurring). For example, a naturally-occurring polynucleotide present in a living animal is not isolated, but the same polynucleotide, separated from some or all of the coexisting materials in the natural system, is isolated.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, the term "treating" includes alleviation of the symptoms associated with a specific disorder or condition and/or preventing or eliminating said symptoms.

As used herein an "effective" amount or a "therapeutically effective amount" of a drug refers to a nontoxic but enough of the drug to provide the desired effect. The amount that is "effective" will vary from subject to subject or even within a subject overtime, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein the term "patient" without further designation is intended to encompass any warm blooded vertebrate domesticated animal (including for example, but not limited to livestock, horses, cats, dogs and other pets) and humans receiving a therapeutic treatment with or without physician oversight.

The term "inhibit" defines a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

Detailed Description

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with one embodiment a pharmaceutical composition is provided comprising a compound of the general structure of Formula I:

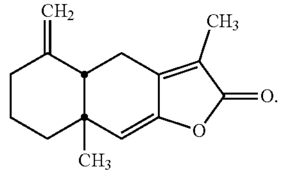

In one embodiment the composition comprises purified atractylenolide I. In one embodiment the composition is further combined with one or more immune checkpoint inhibitors such as an anti-PD-1, anti-PD-L1, or anti-CTLA-4 antibody. In one embodiment a composition comprising a compound of Formula I is administered to a cancer patient in conjunction with an anti-cancer immunotherapeutic treatment. In one embodiment the cancer to be treated is a solid tumor cancer, including for example, colorectal cancer.

In some embodiments, a method comprising contacting a cancer cell with a small molecule is taught, wherein the small molecule comprises ATT-I, and wherein the cancer cell becomes more sensitized to the cytotoxic effects of a CD8+ T-cell.

In some embodiments, the ATT-I is provide alone. In some embodiments, the ATT-I is substantially pure, about 98% pure, about 97% pure, about 96% pure, about 95% pure, about 94% pure, about 93% pure, about 92% pure, about 91% pure, or about 90% pure.

In some embodiments, the ATT-I is provided in combination with other therapeutics, antibodies, or small molecules. In some embodiments, the other therapeutics include PD-1, PD-L1, or CTLA-4. In these embodiments, the PD-1, PD-L1, or CTLA-4 are useful, in part, to help the CD8+ T-cell destroy the cancer cell.

In some embodiments, the cancer cell is capable of forming a tumor. In some embodiments, the cancer cell is from a renal cancer. In some embodiments, the cancer cell comes from colon cancer.

As used herein, the term "sensitizing" means that after contact with the ATT-I, the cancer cell begins to produce and display antigens in an amount capable of being recognized by a CD8+ T-cell.

The chemical structure of Icariine is as follows:

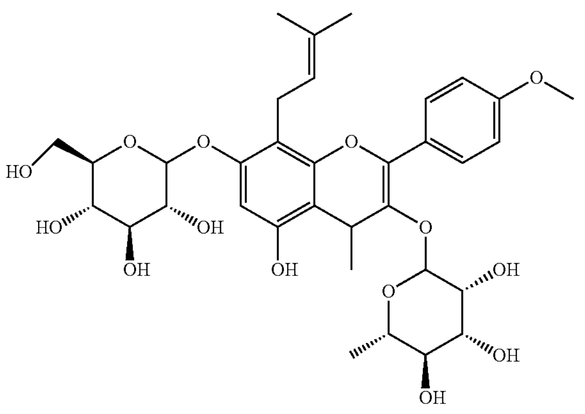 [SMILES: COc1ccc(C2=C(OC3O[C@@H](C)[C@H](O)[C@@H](O)[C@H]3O)C(C)c3c(O)cc(OC4O[C@H](CO)[C@@H](O)[C@H](O)[C@H]4O)c(CC=C(C)C)c3O2)cc1]

The chemical structure of Biochanin A is as follows:

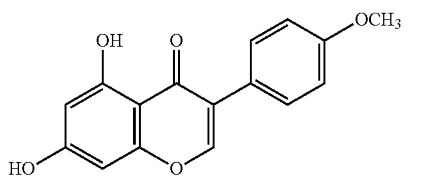 [SMILES: COc1ccc(-c2coc3cc(O)cc(O)c3c2=O)cc1]

Four biologically distinct cell cultures were prepared and two were treated with DMSO (Control) and two were treated with ATT-I (Treatment). Following lysis of each cell pellet, resulting protein solutions were divided into six identical aliquots (50 μL) and equilibrated at six temperature points-35.0; 45.3; 50.1; 55.2; 60.7; and 74.9° C. for 3 minutes as described in the Methods. Resulting denatured proteins of each tube were next pelleted out and the supernatant fractions were sequentially subjected to the following procedures: proteolytic digestion (trypsin/Lys-C based), peptide labelling with different isobaric tags (TMT: Tandem Mass Tags), mixing, and high-pH solvents based reversed phase fractionation. All the fractions were analyzed using nanoLC-MS/MS as described in the Methods. All resulted files were analyzed using the MaxQuant software suite 1.6.0.16. to identify and quantify protein abundance values and JMP® Pro 14.0.0 (64 bit) to generate sigmoidal protein melt curves and subsequent data analyses to screen out potential targets of ATT-I as described in the Examples.

The disclosure will be more fully understood upon consideration of the following non-limiting Examples.

EXAMPLE 1 STUDY DESIGN

The initial goal of this study was to identify natural small-molecule compounds from herbal medicine that increase the responsiveness of colorectal cancer (CRC) cells to CD8+ T-cell mediated cytotoxicity. Two criteria were used for the screen: 1) candidate drugs have no or minimal toxicity on tumor and T cells, a feature distinct from chemotherapeutic drugs; 2) they empower the cytotoxicity of CD8+ T cell against tumor cells. Atractylenolide I (ATT-I) was identified to meet these two criteria from a library of 594 compounds. Using 2D co-cultures and 3D tumor organoid models, in vitro T cell cytotoxicity assays were conducted to determine the effect of ATT-I on the anti-tumor activity of CD8+ T cells. To identify molecular targets of ATT-I in colorectal cancer cells, mass spectrometry-based cellular thermal shift assay (CETSA) was applied on over 13,000 proteins in the lysates of MC38 tumor cells treated with DMSO or ATT-I (5.0 μM).

Psmd4, a functional component of immunoproteasome, was identified as one of the most potential binding targets of ATT-I. The interaction of ATT-I with Psmd4 was confirmed by microscale thermophoresis (MST) binding assay. The effect of ATT-I treatment on the immunoproteasome activity was tested using distinct protease substrates for constitutive 26S proteasome and specific immunoproteasome. To test whether the ATT-I treatment enhances the efficacy of immune checkpoint blockade therapy, syngeneic tumor models in immunocompetent mice were established using subcutaneous and orthotopic cecal wall implantation of MC38 cells (in C57BL/6 mice) and CT26 cells (in BALB/c mice).

All animal studies were approved by the Indiana University School of Medicine committee on animal care (protocol #11269) and were conducted in compliance with institutional and national policies. Seven days post tumor implantation, mice were randomly allocated into four different treatment groups: vehicle control, ATT-I (50 mg/kg, daily), PD-1 antibody (200 μg/mouse, 3 times/week, 5 times in total), and ATT-I+PD-1 combo. Subcutaneous tumor growth was monitored by size and tumor weight at the endpoint of study. Orthotopic tumor growth was monitored by in vivo bioluminescent tumor imaging using IVIS Spectrum after intraperitoneal injection of luciferin. Next, the effects of ATT-I treatment on the immune profiles in CRC tumors were analyzed by CyTOF.

To further determine the immune cell type responsible for the anti-tumor effect of ATT-I, the in vivo experiments with depletion of CD4 T cells (anti-CD4), CD8 T cells (anti-CD8), B cells (anti-CD20), or control (isotype antibody) were conducted. As the main effects of ATT-I were mediated through CD8 T cells, we next applied scRNA-seq analysis of colorectal tumor samples from the mice treated with control, ATT-I, PD-1 antibody, or ATT-I+PD-1 combo, to further assess the CD8 T-cell functions under each conditions. In the t-SNE plot analysis of the scRNA-seq data, types of cells in the tumors were assessed by their gene expression signatures. Finally, patient-derived tumor organoids (PDOs) from human patient CRC samples were established to determine whether treatment of tumor organoids with ATT-I affects the cytotoxicity of autologous CD8 T cells. The PDOs were co-cultured with the preactivated autologous CD8 T cells. Spheroids dissociation and T cell cytotoxicity were assessed by PDO size and number as well as tumor cell death

EXAMPLE 2 MICE AND CELL LINES

C57BL/6 and BALB/c mice, 6-8 weeks old, were purchased from Jackson Laboratory and housed under pathogen-free conditions. OT-I mice (C57BL/6-Tg (TcraTcrb) 1100Mjb/J) were purchased from Jackson Laboratory and bred in-house. All mice were housed in the animal facility of Indiana University School of Medicine. All procedures were carried out in accordance with approval of the Indiana University Institutional Animal Care and Use Committee protocol. MC38 cell line was obtained from Dr. Patrick Hwu, MD Anderson Cancer Center and CT26, SW837 and HCT116 cell lines were obtained from ATCC. MC38, HCT116 and SW837 cells were maintained in DMEM medium supplemented with 10% fetal bovine serum (FBS, Sigma-Aldrich) and 1% penicillin-streptomycin solution (10,000 units/ml penicillin+10,000 μg/ml streptomycin, HyClone). CT26 cells were maintained in RPMI medium supplemented with 10% fetal bovine serum and 1% penicillin-streptomycin solution. Cell lines were cultured at 37° C. in a humidified incubator with 5% $CO_2$.

EXAMPLE 3 REAGENTS

The following antibodies were used: Western blotting antibodies including S5a/PSMD4 (3336S, Cell Signaling), and anti-β-actin (sc-8432, Santa Cruz); immunofluroscence staining antibodies including anti-human HLA-A,B,C (ab70328, Abcam) and anti-EGFR (#4267, Cell Signaling); immunohistochemical staining antibodies including anti-CD8a (98941S, Cell Signaling), anti-F4/80 (70076S, Cell Signaling) and anti-CD4 (25229S, Cell Signaling); flow cytometry antibodies including H2 kb-PerCPCy5.5 (Clone μF6-88.5; Biolegend), CD45-BV605 (Clone 30-F11; Biolegend), TCRB-PE/Cy7 (Clone H57-597; Biolegend), CD11b-eFluor450 (Clone M1/70; eBioscience), CD4-AF700 (Clone GK1.5; Biolegend), CD8-APC/Cy7(Clone 53-6.7; Biolegend), 7-AAD (Biolegend), H-2kd-APC (Clone SF1-1.1; Biolegend), Isotype Mouse IgG2a-APC (Clone MOPC-173, Biolegend) and HLA-A,B,C-APC/Cy7 (Clone W6/32, Biolegend); BioXCell antibodies including anti-mouse PD1 (clone RMP1-14; BE0146), anti-mouse CD4 (clone GK1.5; BE0003-1), rat IgG2a isotype control (Clone 2A3, BE0089), anti-CD20 (Clone AISB12, BE0302), anti-CD8 (Clone 53-6.72; BE0004-1). The dilution of the antibodies was done using the pH 7.0 dilution buffer (BioXcell). ATT-I (B20054; CAS #73069-13-3) was purchased from Yuanye Biotechnology Co. (China).

EXAMPLE 4 TUMOR IMPLANTATION AND TREATMENT

For the orthotopic injection of MC38 colorectal cancer cells in the caecum, mice were anaesthetized and shaved around the belly. To expose the caecum we made a small incision of the skin and muscle. MC38 cells expressing luciferase were injected in a final volume of 50 μl PBS containing $2\times10^5$ cells using a 30 Gauge Needle. The caecum was repositioned in the mice and the wound was closed using surgical sutures and wound clips. For subcutaneous tumor experiments $1\times10^5$ MC38 cells or $5\times10^4$ CT26 cells were injected in a final volume of 50 μl PBS using a 30 Gauge Needle. Mice were randomly allocated into the different groups 7 days post tumor implantation. Anti-PD1 or isotype control treatment was administered intraperitoneally 3 times per week for a total of 5 injections at 200 μg/mouse. ATT-I was administered intraperitoneally every day at 50 mg/kg bodyweight. For the depletion experiment anti-CD4, anti-CD8, anti-CD20 and isotype antibodies were administered three times per week. The antibodies were administered two days prior to tumor cell inoculation and the injection continued until the end of the experiment. Orthotopic tumor growth was monitored by in vivo bioluminescent tumor imaging using IVIS Spectrum after intraperitoneal injection of 200 μl of 15 mg/ml luciferin (Potassium Luciferin; Gold Biotechnology, MO, USA). The fluorescence signal was acquired 15 min after the substrate administration.

EXAMPLE 5 CYTOF SAMPLE PROCESSING AND DATA ANALYSIS

Tumors were excised and manually cut to 2 mm×2 mm pieces. They were then both enzymatically and mechanically dissociated according to the manufacturers' procedures using the mouse tumor dissociation kit and GentleMACS Dissociator (Miltenyi Biotec). The cells were further filtered using a 100 micron filter (BD Falcon). After centrifugation the red blood cells were lysed (Biolegend), neutralized, washed and resuspended in house made CyTOF buffer (cold PBS containing 0.5% BSA and 0.02% Azide). For each sample $1.5\times10^6$ cells were used. CyTOF data were evaluated via viSNE analysis using the Cytobank platform (36). viSNE analysis allows the visualization of a high dimensional analysis in two dimensions using the Barnes-Hut implementation of the t-Distributed Stochastic Neighbor Embedding (tSNE) algorithm. We ran the viSNE analysis on the samples through a proportional sampling, with 7500 iterations, a perplexity of 30 and a theta of 0.5. On this viSNE analysis we performed SPADE clustering. The cell populations were then manually gated on the SPADE tree based on the selected markers. Hereafter, these clustered cell populations were visualized on viSNE as an overlaid plot.

EXAMPLE 6 MICROSCALE THERMOPHORESIS ANALYSIS

Purified Psmd4 protein was labeled with Alexa-647 (Thermo Fisher, A20173). Compounds was titrated between 1 nM to 500 uM to a constant amount of Alexa-647 labeled Psmd4. The samples were incubated at room temperature for 10 min before the measurements. The binding assay was performed in a buffer with 20 mM Tris, 100 mM NaCl and 0.02% Tween-20. A NanoTemper Monolith Instrument (NT.115) was used for measuring thermophoresis. Standard capillaries (cat #K002, Nanotemper) were used in the experiments. Thermophoresis of the protein in presence of compound was analyzed for 30 seconds. Measurements were performed at room temperature.

EXAMPLE 7 THREE-DIMENSIONAL PROTEIN STRUCTURE ANALYSIS

The PyMol graphics program was used to depict three-dimensional structures. The Schrodinger drug discovery package was used to predict the structure of the covalent complex between ATT-I and Psmd4. The Maestro module within Schrodinger was used to process the protein structures. Hydrogen atoms were added and the protonation state of ionizable residues assigned by pro-pKa. The structure was energy minimized. The CovDock module was used for the covalent docking of ATT-I to Psmd4.

EXAMPLE 8 GENERATION OF MURINE AND HUMAN PATIENT-DERIVED TUMOR

MC38 OVA tumors and human colorectal cancer samples (obtained using an approved institutional protocol and patient consent) were cut to small pieces (3 mm×3 mm), processed into small pieces using the MACS Dissociator (Miltenyi Biotec) and digested to single cells using the mouse or human tumor isolation kit, respectively, according to manufacturer's guidelines (Miltenyi biotec). The isolated cells were cultured overnight with F12/DMEM, 10% FBS culture medium, supplemented with 1% Penicillin-Streptonmycin and 150U/ml murine IL2 (#575402, Biolegend) or human IL2 (#589102, Biolegend). Adherent cells were harvested to generate organoids. For human clinical samples, the CD8+ T cells were also enriched by anti-human CD8+ T cell beads and stimulated by the human T-activator CD3/CD28 Dynabeads (Milenyi Biotec). The CD8+ T cells were expended in the F12/DMEM, 10% FBS culture medium. The adherent cells were suspended with a concentration of $2\times10^5$ cells/ml in the HICS minus Wnt culture medium containing 10% Matrigel Basement Membrane Matrix (Corning, 356255), which has been reported for generation of colorectal tumor organoids (37). The cells were seeded in a 6-well culture plate with ultra-low attachment surface (Corning) with a total volume of 2 ml per well. The cells were cultured for one week to generate organoids. Every 2-3 days culture medium was added with same volume and split in two wells. The murine organoids with diameter of 70-150 μm were filtered sequentially by 70 μm and then 150 μm cell strainers (70 μm, Fisher Scientific, #07201431; 150 μm, pluriStrainer, #43-50150-03). The MC38 OVA organoids were treated with and without drug for 48 hours and then were co-cultured with the CD3/CD28 bead-activated CD8' T cells isolated from OT-I mouse for 24 hours. The patient-derived tumor organoids were co-cultured with autologous CD8' T cells. The organoids were imaged under optical microscope, digested into single cells and analyzed by flow cytometry. The organoid size was analyzed using image J software 1.50e.

EXAMPLE 9 PSMD4 PROTEIN EXPRESSION AND PURIFICATION pGEX-6P-1 vector was used to clone the recombinant protein GST-Psmd4. Mouser PSMD4 cDNA fragment (NM_001330692.2.) was amplified and ligated into the pGEX-6P-1 vector (Addgene). In order to get the recombinant protein, pGEX-6P-1/PSMD4 was transformed into *E. coli* BL21 (DE) (BioLab, UK). The positive clone was cultured in LB medium until OD600 reached approximately 0.6 at 37° C. Isopropyl β-d-1-thiogalactopyranoside (IPTG, Sigma) was used to induce protein expression with the final concentration of 1 mM for 5 h at 37° C. The cells were harvested and suspended in the binding buffer (140 mM NaCl, 2.7 mM KCl, 10 mM Na2HPO4, 1.8 mM KH2PO4, pH 7.3). The cells were lyzed by sonication for 30 min, and then the cell debris was removed by centrifugation at 12,000 rpm for 20 min at 4° C. The supernatant was collected and applied to a Glutathione Sepharose 4 FF column (Sigma, USA) to purify recombinant protein according to the manufacturer's instructions. GST-tag was digested by Prescission protease (Sigma, USA) to purify Psmd4 proteins without tag.

EXAMPLE 10 CD8' T CELL CYTOTOXICITY ASSAY

To generate mature cytotoxic T cell (CTL), splenocytes were isolated from OT-I mice and stimulated with 5 μg/ml OVA257-264 (S7951-1 MG, Sigma) in the presence of 2 ng/ml IL-2 for 3 days. T cells were then centrifuged and cultured in RPMI1640 medium containing of 2 ng/ml murine IL2, 10% FBS and 1% PS.To measure the cytotoxicity of CD8+ T cells, 50,000 enriched CD8+ T cells were mixed in 96-well plates with MC38-OVA cells at ratios of 5:1, 1:1 or 1:5. ATT-I was added to MC38 cells or CD8+ T cells 48 hours before co-culture. We assessed the killing efficiency by measuring the activity of luciferase (#E1910, Dual-Luciferase® Reporter Assay System, Promega) after 6 hours of co-culture of the T-cells together with the tumor cells.

EXAMPLE 11 PSMD4 SHRNAS AND MC38 CELLS WITH STABLE PSMD4 KNOCKDOWN

Two PSMD4 shRNAs were used for PSMD4 knockdown: PSMD4 shRNA #1:

```
PSMD4 shRNA #1:
                                        (SEQ ID NO. 1)
5'-CCGGTTATAGAACAGGGTCACATTGCTCGAGCAATGTGACCCTGTTC

TATAATTTTTG-3'.

PSMD4 shRNA #2:
                                        (SEQ ID NO. 2)
5'-CCGGGTGAATGTTGACATCATTAATCTCGAGATTAATGATGTCAACA

TTCACTTTTTG-3'.
```

Lentiviral PSMD4 shRNA was transduced into MC38 cells. 48 hours after infection, the MC38 cells were cultured with the addition of 2 μg/ml puromycin and the survived cells were grown up to single colonies, from which the colonies with stable knockdown of PSMD4 (PSMD4 expression determined by q-PCR) were selected for the in vivo.

EXAMPLE 12 IMMUNOPROTEASOME ASSAY

Using the immunoproteasome actitivty fluoremetric assay (UBPBio, Cat J4170), we determined the chymotrypsin-like, trypsin-like and caspase-like activities of MC38 and MC38-PSMD4 loss tumor cells treated with DMSO control or 5 μM ATT-I treatment. After 24 hours of treatment, cell lysates were obtained. The respective immunoproteasome cleavage capacity upon exposition to each of the substrates was determined using the AMC fluorescence detected at the 360 nm excitation and 460 nm emission wavelength. The incubation periods and substrates were used according to the manufacturer's guidelines.

EXAMPLE 13 IMMUNOFLUORESCENCE

Immunofluorescence was performed as described previously (38). In Brief, cells (5×103 per well) were seeded and cultured overnight to Millicell EZ 8-well glass slides, rinsed with PBS and fixed with 4% paraformaldehyde (PFA) for 10 min at room temperature. Fixed cells were incubated with 0.5% Triton X-100/PBS and blocked with 0.2% BSA/PBS. Cells were then incubated with primary antibody (anti-HLA-A,B,C) overnight at 4° C. followed by Alexa Fluor 488-conjugated goat anti-mouse IgG antibody (dilution 1:300) for 1 hour at room temperature. DAPI (Sigma-Aldrich) staining was performed after antibody staining. Samples were mounted with mounting medium (Sigma-Aldrich) and fluorescent images were taken using Leica TCS SP8 (upright high-speed multiphoton) confocal imaging system. 3-D models were built and analyzed with Imaris ×64 8.1.2 software. For 3-D imaging, Imaris microscopy image analysis software v8.0 were used to build-up the 3-D models.

EXAMPLE 14 SINGLE-CELL RNA SEQUENCING (SCRNA-SEQ) ANALYSIS

Single cell suspension of tumors is prepared as for the CyTOF samples. Hereafter, the single cells were stained for: CD45-BV605, TCRB-PE/Cy7, CD11b-eF450, CD4-AF700, CD8-APC/Cy7 and 7-AAD. Viable (7-AAD negative) single cells were sorted as CD45, CD11b", TCRB. The sorted samples were immediately submitted to the core facility for sample preparation for the scRNA sequencing. The library for downstream scRNA sequencing is constructed using 3' v2 library preparation kit following manufacturer's protocol (10× genomics). After amplification and normalization, cDNA with index barcode were loaded on and sequenced by NovaSeq 6000 (Illumina).

Sequencing data were demultiplexed and mapped to mm 10 genome for the retrieval of gene expression counts matrix by utilizing Cell Ranger (10× Genomics). Downstream analysis of these matrices were conducted by Seurat (V3.1), unless indicated otherwise. Cell filtering follows two criteria for all samples: 1) detected number of RNA in a single cell should be over 500, 2) the percentage of mitochondria genes detected in a single cell should not exceed 15%. The remaining cells from each sample were merged and log-normalized. PhenoGraph in Seurat was applied to cluster cells with resolution set as 0.5. Low dimensional t-SNE visualization was computed by Rtsne package using normalized transcriptional expression profile with perplexity setting as 30. Each cell cluster is annotated by marker genes found by FindAllMarkers function in Seurat. Heatmap is then drawn with log-normalized expression level. We further looked into T-cell activation and cytotoxicity level on representative genes with dot visualization. The color code of each codes stands for the relative mean expression level from different sample, and the size of each dot represents the percentage of expressed cells within samples. To evaluate the cytotoxic level of each cell, we used the averaged expression level of six cytotoxic and CD8+ T cell marker genes, namely: Prfl, Ifng, Tnf, Pdcdl, Sla2 and Cd8a. Significant expression of each cytotoxic marker gene in each cell were computed by using left truncated mixture Gaussian model. CD8+ effector T cells with significant cytotoxic genes expressed were defined by the CD8+ effector T cells with at least three out of the six genes significantly expressed, the proportion of which was further computed.

EXAMPLE 15 MASS SPECTROMETRY (MS) BASED CELLULAR THERMAL SHIFT ASSAY (CETSA) TO IDENTIFY POTENTIAL TARGETS OF ATT-I IN MC38 CELLS USING MELT TEMPERATURE (TM) SHIFTS

To screen out potential binding targets for ATT-I in a high throughput fashion, two groups of cells were compared for their protein level temperature dependent denaturation profiles using two biologically distinct replicate cell cultures for each group. Briefly, the two groups were 1) DMSO treated control MC38 cells; and 2) ATT-I (5.0 μM) treated MC38 cells. Sample preparation, mass spectrometry analysis, bioinformatics and data evaluation were performed in collaboration with the Proteomics Core Facility at the Indiana University School of Medicine Methods described below in brief were adaptations from previously published reports (39-43) and vendor provided protocols.

EXAMPLE 16 CELL LYSIS AND PROTEIN ASSAY

For cell lysis, a fresh solvent system (10 mL) was first prepared to include 50 mM HEPES, 200 mM NaCl, 10 mM $MgCl_2$.5 mM β-glycerophosphate, 0.1 mM activated sodium orthovanadate, 2 mM TCEP (tris(2-carboxyethyl) phosphine hydrochloride) and 1× EDTA-free protease inhibitor (complete Mini, Roche). Pelleted cells were then mobilized in this solvent buffer system (800 μL) contained in 1.5 mL Micro Tubes (TPX Plastic for Sonication from Diagende Inc.). Mobilized cells were next subjected to sonication using a Bioruptor® sonication system (Diagende) 30 seconds/30 seconds respective on/off cycles for 15 mins in a 4° C. cold water bath. Total protein concentration of each sample was t determined using a Bradford protein assay. All lysates were then diluted to a protein concentration of 2 μg/μl for the subsequent temperature treatment.

EXAMPLE 17 TEMPERATURE TREATMENT, SUPERNATANT "DECANTING", AND PROTEOLYTIC DIGESTION

Six aliquots (50 μl) of each sample treated with either DMSO or compound were placed among six tubes designed for PCR workflows, and equilibrated at six temperature points-35.0; 45.3; 50.1; 55.2; 60.7; and 74.9° C. for 3 mins in a thermocycler (Mastercycler Pro, Eppendorf) system as described elsewhere (39, 41). Following heat treatment, lysates were centrifuged for 20 mins at 4° C. to pellet out insoluble protein and then to decant the soluble fraction. A 45 μL aliquot from each heat-treated sample was subject to protein precipitation and then reconstituted in 30 μL of 8 M Urea in Tris.HCl (pH 8.0). Samples were next subjected to reduction of Cys-Cys bonds with 5 mM TCEP, and alkylation with 10 mM chloroacetaminde (CAM) to protect the reduced Cys residues. Samples were diluted to have 2 M Urea and were digested in-solution overnight using Trypsin (Promega) to derive peptides.

EXAMPLE 18 ENRICHMENT OF PEPTIDES

Resulting peptides were "de-salted" using Sep-Pak® Vac 1cc C18 Cartridges, 50 mg Sorbent per Cartridge, 55-105 μm Particle Size (Waters Co.) employing a vacuum manifold. Briefly, columns adapted onto the extraction manifold were first washed sequentially with (1) ACN (500 μL)-two times, (2) ACN/$H_2O$ 70/30 (v/v; $_{0.1}$% FA; 200 μL)-one time, and (3) MS-grade water (500 μL)-two times. Peptides from each "digestion" solution were then subjected to immobilization on C18 material by a gentle application of vacuum into the extraction manifold vacuum chamber to move each solution three times by collecting the "flow-through" fractions and running them again on to the same column. Next, the peptide-bound C18 columns were washed with 500 μL of MS-Grade $H_2O$ and then eluted by passing 150 μL of ACN/$H_2O$ 70/30 (v/v; 0.1% FA) three times. All elution fractions were collected into 1.5 mL Eppendorf tubes and subjected to complete dryness using a speed vacuum system.

EXAMPLE 19 TANDEM MASS TAGS (TMT) BASED PEPTIDE LABELLING AND FRACTIONATION

The respective dried samples were then subjected to TMT-based labelling using sixplex kits (TMT6plex™ Isobaric Label Reagent Set, 2×0.8 mg). The TMT channels-TMT126, TMT127, TMT128, TMT129, TMT130, and TMT131, were employed to label peptide solutions derived from the 35.0; 45.3; 50.1; 55.2; 60.7; and 74.9° C. temperature treatments. Briefly, each dried sample (equivalent of 10 μg of protein digest) was reconstituted in 100 μL of 50 mM Triethylammonium bicarbonate (TEAB) and dry labeling reagents were dissolved in 40 μL of acetonitrile (ACN). Reconstituted peptide solutions were then mixed with 40 μL labelling reagent solution and kept at room temperature for overnight to label the peptides. Labelling reaction was next quenched by adding 8 μL of 5% hydroxylamine and keeping the reaction mixture at room temperature for more than 15 mins. Labelled peptide solutions were next mixed together and subjected to complete dryness in a speed vacuum system. Dried labelled peptide mixtures were fractionated using reversed phase fractionation columns (8 fractions) employing vendor provided protocols (Pierce Biotechnology). The resulting 8 fractions were dried using a speed vacuum system and re-constituted in 0.1% formic acid (30 μL) prior to nano-LC-MS/MS analysis.

EXAMPLE 20 NANO-LC-MS/MS ANALYSIS

Nano-LC-MS/MS analyses were performed on a Q-Exactive Plus™ mass spectrometer (Thermo Scientific) coupled to an EASY-nLC™ HPLC system (Thermo Scientific). Ten uL equivalent volume of the re-constituted fractions from above were loaded using 300 bar as applied maximum pressure onto an in-house prepared reversed phase column. Each reversed phase column was prepared by pulling a 100 μm fused-silica column to carry 5 μm tip for the nanospray using a P-2000 laser puller, and then packing the capillary with C18 reverse phase resin (particle size: 3 μm diameter; Dr. Maisch HPLC GmbH). The peptides were eluted using a varying mobile phase (MP) gradient from 95% phase A (FA/$H_2O$ 0.1/99.9, v/v) to 24% phase B (FA/ACN 0.4/99.6, v/v) for 150 mins, from 24% phase B to 35% phase B for 25 mins and then keeping the same MP-composition for 5 more mins at 400 nL/min to ensure elution of all peptides. Nano-LC mobile phase was introduced into the mass spectrometer using a Nanospray Flex Source (Proxeon Biosystems A/S). The heated capillary temperature was kept at 275° C. and ion spray voltage was kept at 2.5 kV. During peptide elution, the mass spectrometer method was operated in positive ion mode for 180 mins, programmed to select the most intense ions from the full MS scan using a top 20 method. Additional parameters: Microscans 1; Resolution 70k; AGC target 3E6; Maximum IT 50 ms; Number of scan ranges 1; Scan range 400 to 1600 m/z; and Spectrum data type "profile", and then to perform data dependent MS/MS scans with parameters: Microscans 1; Resolution 35k; AGC target 1E5; Maximum IT 64 ms; Loop count 20; MSX count 1; Isolation window 0.7 m/z; Fixed first mass 100 m/z; NCE 38.0; and Spectrum data type "Centroid". The respective data dependent settings were set with parameters: Minimum AGC target of 1.00e3; Intensity threshold of 1.6e4; Apex trigger as "-"; Charge exclusion as "1,7,8, >8"; Multiple Charge States as "all"; Peptide match as "preferred"; Exclude isotopes as "on"; Dynamic exclusion of 30.0 s; If idle "pick others". The data were recorded using Thermo Xcalibur (4.1.31.9) software (Thermo Fisher)

EXAMPLE 21 DATA ANALYSIS

Resulting RAW files were analyzed using the MaxQuant software suite 1.6.0.16. The MS/MS spectra were searched against in silico tryptic digest of *Mus musculus* proteins database (FASTA format) from the UniProt sequence database (v. May 2017). Default MaxQuant parameter settings were utilized as downloaded from www.maxquant.org, except for the following: 1) in group specific parameters tab to have "type" as "Reporter ion MS2"; "Isobaric labels" selected as "6plex TMT"; "Reporter mass tol." as "0.003 Da"; 2) in group specific parameters-"digestion" mode as specific for trypsin with maximum 3 missed cleavages; 3) group specific parameters-"modifications" to have variable modifications acetyl(protein N-terminus); phosphor (STY) and methionine oxidation, with peptides to carry maximum number of 5 modifications per peptide; and 4) global parameters tab-to carry a minimum peptide length of 7 residues, maximum peptide mass of 4600 Da. Please note, 4 such searches were carried out separately for each of four samples. The resulting Maxquant "peptides.txt" files were then imported to Microsoft Excel™ (Version 14.07182.5000, 32-bit) and then to JMP® 12.1.0 (64 bit, Microsoft Windows 7 Enterprise 64-bit, Service Pack 1, Copyright@2015 SAS Institute Inc.) for processing. Only those peptides identified with a minimum of PEP value of 0.05 were selected for further evaluation. Protein quantification values were derived by summation of quantification values of only the unique peptides (at least one for one protein). Following methodology was utilized for procedural error correction/normalization of the quantification values obtained for each protein in each experiment.

EXAMPLE 22 STATISTICAL ANALYSIS

Statistical analysis was conducted using GraphPad Prism and R. Comparison of two data sets was done using unpaired student's t-test. Comparison of more than two data sets was done using one-way ANOVA followed by Bonferroni's multiple comparison test. For tumor growth assays, we used two-way ANOVA followed by Tukey's multiple comparisons test. The results are displayed as the mean±SD or +SEM. Kaplan-Meier plots are used for survival curves and analyzed using the Log-rank test. The number of asterisks indicates the level of significance: *, $p<0.05$; , $p<0.01$; *, $p<0.001$ and ****, $p<0.0001$. For the scRNA-seq, downstream analysis of those matrices were conducted by Seurat (V3.1). Cell filtering follows two criteria for all samples: 1) detected number of RNA in a single cell should be over 500, 2) the percentage of mitochondria genes detected in a single cell should not exceed 15%. The remaining cells from each sample were merged and log-normalized. PhenoGraph in Seurat was applied to cluster cells with resolution set as 0.5. Low dimensional t-SNE visualization was computed by Rtsne package using normalized transcriptional expression profile with perplexity setting as 30. Each cell cluster is annotated by marker genes found by FindAllMarkers function in Seurat. Significant expression of cytotoxic marker genes in each CD8+ T cell were computed by using left truncated mixture Gaussian model. Statistical analysis for CETSA was described in detail and included in the Methods.

EXAMPLE 23 ATT-I IS A NATURAL SMALL CHEMICAL COMPOUND THAT PROMOTE CD8+ T CELL-MEDIATED TUMOR CELL KILLING

Figure 1E:
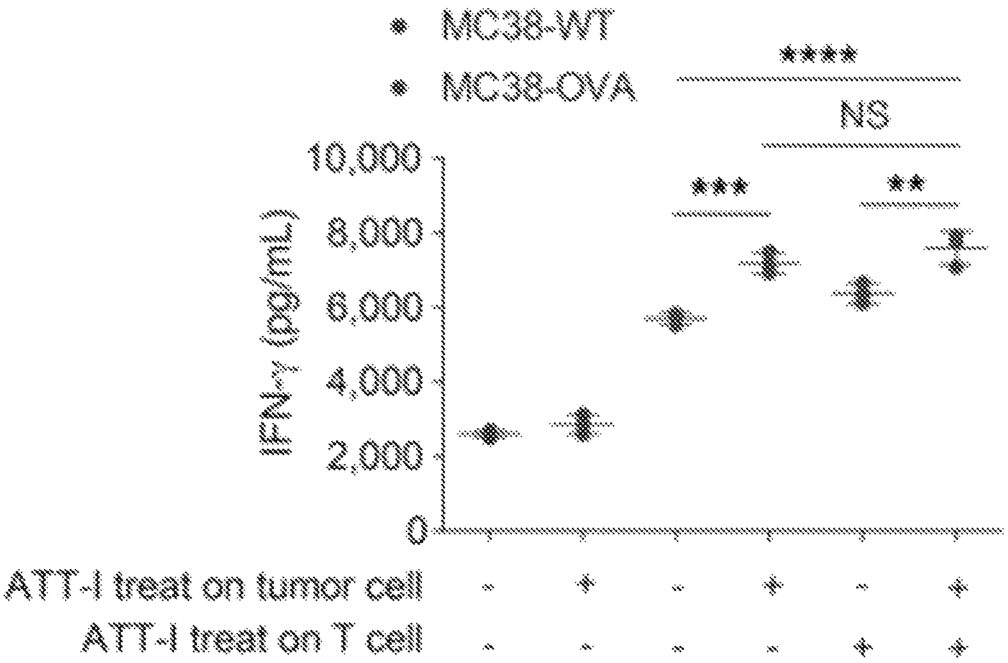
Figure 1F:
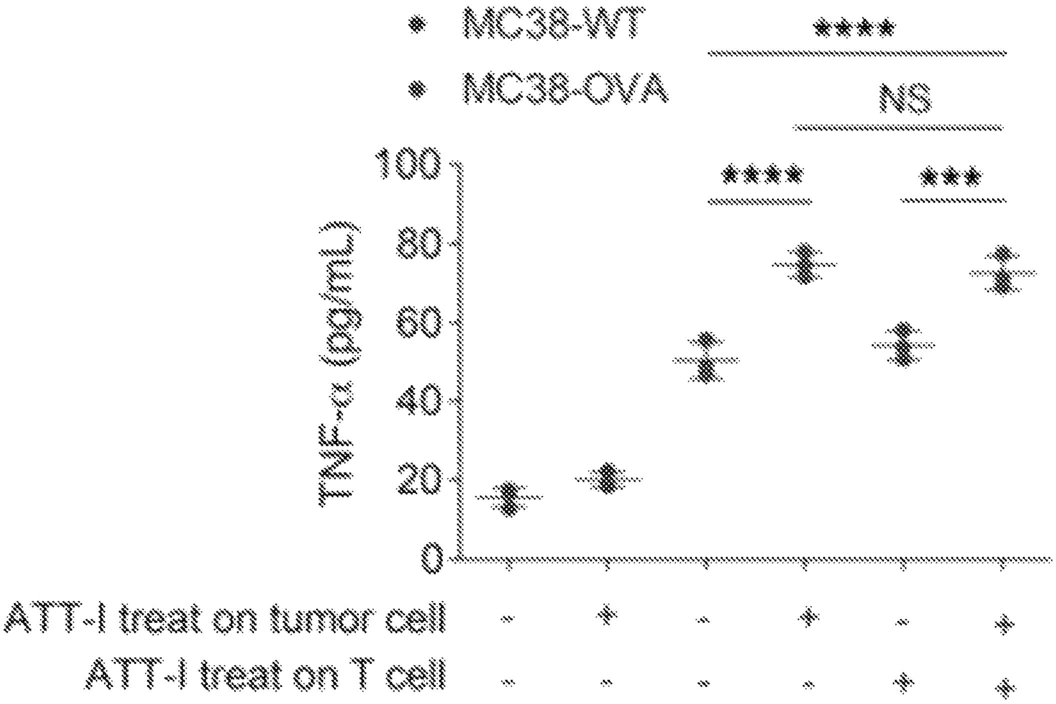

To identify small molecular compounds for improving the CD8+ T cell-mediated killing of colorectal tumor cells in vitro, we screened a library containing 594 small molecular compounds purified from over 500 herbal medicinal plants that have been widely used in traditional Chinese medicine (table of compounds not shown). The screen system includes a mouse colorectal tumor cell line MC38 stably expressing OVA257-264 (an MHC class I-restricted peptide epitope of chicken ovalbumin) and CD8+ T cells that are MHC class I-restricted and express OVA-specific TCR. The CD8+ T cells were freshly isolated from the spleen of OT-I mouse (C57BL/6-Tg (TcraTcrb) 1100Mjb/J). To exclude the compounds with cytotoxic activity similar to that of chemotherapeutic drugs, we first assessed their cytotoxicity on both the CD8+ T cells and tumor cells (FIG. 1A). The 449 compounds with minimum to low cytotoxicity on both T and tumor cells (>80% of viability in vehicle-treated cells) were sorted out for the next screen of antigen-specific OT-I CD8+ T-cell killing of MC38-OVA tumor cells using an in vitro luciferase assay. Three top-ranked compounds that most potently affected the T-cell activity are icariin, biochanin A, and atractylenolide I (FIG. 1B). Their activities were validated in the T cell cytotoxicity assays with the ratios of T cells versus tumor cells ranging from 5:1 to 1:5 (FIG. 1C). As atractylenolide I (ATT-I) exhibited the most potent activity, we chose to further identify its mechanism of action. Upon pretreatment of either CD8+T cells or the tumor cells separately, we found that ATT-I enhanced tumor-killing effects in a way dependent on the tumor cells, but not on the CD8+ T cells as the treatment of CD8+ T cells only did not have notable effect on their cytotoxicity (FIGS. 1D and 1E). To further confirm the activity of ATT-I, we generated 3D tumor organoids derived from MC38-OVA tumors and co-cultured them with OT-I cells (FIG. 2). With the treatment of ATT-I, the tumor organoids exhibited markedly enhanced killing from the OT-I cells in comparison with that of the untreated organoids. However, this treatment had no notable effect on the organoids without addition of OT-I cells. Collectively, the results suggest that the ATT-I treatment increases the immunogenicity of the tumor cells.

EXAMPLE 24 ATT-I INTERACTS WITH THE IMMUNOPROTEASOME COMPONENT PSMD4

ATT-I is one of the major bioactive ingredients isolated from the rhizomes of Atractylodes *macrocephala*. Previous studies have reported various pharmacological activities of ATT-I, including anti-inflammation, neuroprotective activity, and anti-tumor activity. However, apart from the reported bioactivities, molecular targets of ATT-I and relevant mechanisms of action have yet to be determined. Due to the chemical structure of ATT-I, it is technically difficult to identify its protein targets by direct biochemical methods such as affinity pulldown assay. Here, we conducted a mass cytometry screening assay based on melt temperature shifts, referred to as cellular thermal shift assay (CETSA), on MC38 tumor cells treated with or without ATT-I. The CETSA approach is established on the same principle as conventional thermal shift assays, in that target proteins of a small molecule compound display an altered melting curve when exposure to increased temperature, and that drug binding leads to significant thermal stabilization or destabilization of potential target proteins. Control and ATT-I-treated MC38 tumor cell lysates were heated to different temperatures (32° C. to 75° C.). Detectable proteins in the soluble fraction of cell lysates were quantified by mass spectrometry and their melting temperature shifts were determined. Among the top potential protein targets (Cggbp1, Sorbs3, Copb1, and Psmd4) identified from the screen, we validated Psmd4 as a primary target protein of ATT-I from its protein denaturation curves and thermal shift. The proteasome 26S subunit non-ATPase 4 (Psmd4) is an essential component of the 19S regulator lid in the 26S immunoproteasome complex that processes MHC-I-associated antigen peptides. In the immunoproteasome, Psmd4 acts as an ubiquitin (Ub) receptor that mediates recruitment of the ubiquitylated protein for degradation and antigen processing. The altered protein stability and thermal shift of Psmd4 were further validated by western blotting assay on mouse (MC38) and human (HCT116) CRC cells, which showed enhanced Psmd4 protein stability upon ATT-I treatment. To confirm the direct interaction of ATT-I with Psmd4, bacterially expressed mouse Psmd4 was purified and incubated with ATT-I under varying concentrations in the microscale thermophoresis (MST) binding assay. The result showed a notably high affinity of ATT-I to Psmd4 (Kd=0.4 μM) (FIG. 2). Structural analysis of the Psmd4-containing human 26S proteasome predicted a potential binding site near the Cys58 group of Psmd4 for ATT-I. The binding of ATT-I may prevent Psmd7, another regulatory subunit of the proteasome, from interacting with Psmd4. While the functional role of Psmd7 in the immunoproteasome is unknown, we wanted to see if ATT-I promotes the activity of the immunoproteasome in the antigen processing in cancer cells. To verify the activity of ATT-I on the 26S immunoproteasome, we assessed the chymotrypsin-like, trypsin-like and caspase-like activities on the lysates of MC38 cells treated with or without ATT-1. The Ac-ANW-AMC (chymotrypsin substrate), Ac-PAL-AMC (trypsin substrate) and Ac-KQL-AMC (caspase substrate) substrates were incubated with the immunoproteasomes and their cleavage activities were measured by the released AMC fluorescence. The ANW and PAL are preferred substrates for the immunoproteasome while KQL can be cleaved by both the immunoproteasome and constitutive 26S proteasomes. The ATT-I treatment lead to markedly enhanced activities of the immunoproteasome in processing all the three types of substrates. However, knockdown of PSMD4 in the cell abolished the effect of ATT-I, suggesting the ATT-I activity on the immunoproteasome is dependent on PSMD4.

EXAMPLE 25 ATT-I PROMOTES ANTIGEN PRESENTATION AND ENHANCES THE EFFICACY OF CRC IMMUNOTHERAPY

We demonstrated enhanced cleavage activity of the protease substrates by the immunoproteasome upon ATT-I treatment. Consequently, this enhanced immunoproteasome activity could ultimately promote antigen processing and presentation on tumor cells. Tumor antigen presentation to CD8+ T cells are mediated by the MHC Class I complex. We thus assessed the levels of MHC-I on the surface of mouse (MC38, CT26) and human (HCT116, SW837) CRC cells. The result showed that both mouse and human tumor cells displayed increased levels of MHC-I (H-2Kb and H-2Kd for MC38 and CT26, respectively, and HLA-A,B,C for HCT116 and SW837) on the cell surface, indicating increased antigen presentation on the ATT-I-treated tumor cells. Because CD8+ T cells recognize tumor cells through the interaction of MHC-I with the TCR, we reasoned that the enhanced tumor cell recognition would improve the efficacy of the anti-PD-1-based immunotherapy. We therefore assessed the therapeutic responses of CRC tumors to the combinational treatment of PD-1 monoclonal antibodies (mAb) with ATT-I (50 mg/kg) in C57BL/6 and BALB/c mice bearing MC38 and CT26-derived tumors, respectively (FIGS. 4A, 4B and 4C). As for the clinical context, MC38-derived colorectal tumors with high microsatellite instability (MSI-H) responded better to PD-1 treatment, while CT26 tumor-bearing mice, a model for microsatellite stable (MSS) tumors, displayed a low PD-1 therapeutic benefit. Interestingly, in both cases, the addition of ATT-I to the PD-1 blockade treatment resulted in significant tumor growth control, while the ATT-I treatment by itself only had modest effects. The results suggested that ATT-I treatment may promote global antigen presentation of tumor cells regardless of the amounts of tumor neoantigens in MSI-H and MSS tumor cells. Additionally, due to the immunosuppressive tumor microenvironment, CD8+ T cells are often at inactive states, which can be activated by the PD-1 inhibition for better killing of the tumor cells with enhanced antigen presentation. We further validated the enhanced therapeutic benefit for the combination of ATT-I with the PD-1 blockade in the orthotopic MC38 tumor model (FIG. 4D). While the PD-1 mAb treatment notably extended the survival of the tumor-bearing mouse (median survival time 50 days) in comparison with the control mice (median survival time, 30 days) or the only ATT-I-treated mice (median survival time, 35 days), the combination of PD-1 mAb and ATT-I further extended the survival of the tumor-bearing mice with median survival time >150 days. Consistent with previous studies regarding the biosafety of Atractylodes *macrocephala* (1.32 g daily for up to seven weeks) in clinical applications, treatment of ATT-I at the tested doses had no notable toxicity in vivo.

Animal body weights and pathological analysis of major organs did not reveal any substantial differences between the ATT-I-treated group and the control vehicle group, suggesting negligible systemic toxicity of ATT-I. To determine whether the specific targeting of ATT-I on Psmd4 enhanced the therapeutic responses of PD-1 blockade, we treated the mice harboring MC38-PSMD4 loss tumors with PD-1 only or PD-1 in combination with ATT-I (FIG. 4E). The additional benefit from ATT-I in the combination therapy completely disappeared, hereby confirming the specific action of ATT-I through targeting Psmd4.

EXAMPLE 26 ATT-I ENHANCES CD8+ T-CELL INFILTRATION AND CYTOTOXICITY IN CRC IMMUNOTHERAPY

As ATT-I promotes the anti-tumor immune responses in immune checkpoint blockade therapy, we next wanted to define the effects of ATT-I treatment on the immunological changes in CRC tumors. To this end, we harvested colorectal tumors 28 days post orthotopic cecal wall implantation of MC38 cells for the analysis of tumor microenvironment using mass cytometry (CyTOF). Similar to the tumor growth studies abovementioned, the ATT-I treatment significantly enhanced the anti-tumor effects of PD-1 mAb treatment (FIG. 5A). The combination of PD-1 mAb and ATT-I led to a drastically enhanced T-cell infiltration and reduced macrophage infiltration in comparison with single agent treatments of either PD-1 mAb or ATT-I (Table 1), hereby tipping the balance towards a more anti-tumor microenvironment. Further analysis revealed that both CD8+ and CD4+ T cells displayed lower CD69 expression levels upon the combination of ATT-I with PD-1 mAb. The reduced expression levels of CD69 may account for a rescue from T-cell exhaustion, which is also reflected by their enhanced capacity to secrete interferon gamma (IFN-γ).

TABLE 1

Percentages of distinct immune cell populations within the CD45+ infiltrating immune cells in colorectal cancer tumors

| % population | Control | ATT-I | PD1 | Combination |
|---|---|---|---|---|
| B cells | 2.8 | 1.0 | 7.8 | 26.9 |
| CD4+ T cells | 3.5 | 1.9 | 5.1 | 18.5 |
| CD8+ T cells | 4.2 | 3.1 | 8.5 | 14.6 |
| DCs | 2.7 | 4.0 | 5.7 | 3.6 |
| Macrophages | 53 | 41 | 36.2 | 10.2 |
| Mo-MDSC | 19.8 | 24.3 | 18.5 | 11.7 |
| NK cells | 1.1 | 0.9 | 3.2 | 2.0 |
| PMN-MDSC | 10.8 | 20.1 | 11.7 | 8.5 |
| Other | 2.1 | 3.8 | 3.4 | 4 |

To determine the immune cell population responsible for the anti-tumor effect of ATT-I, we depleted mice of B cells, CD4+ T cells or CD8+ T cells (FIG. 5B-5D). The depletion antibodies were administered intraperitoneally before tumor inoculation and every three days thereafter until the end of the experiment. The anti-tumor effect for the combination of ATT-I with PD-1 mAb was completely abrogated upon CD8+T-cell depletion. By contrast, depletion of CD4+ T cells had no notable effect, while B-cell depletion only minimally reduced the anti-tumor effects. As the main effects of ATT-I were mediated through CD8+ T cells, we next applied single-cell RNA sequencing (scRNA-seq) analysis of colorectal tumor samples from the mice treated with control, ATT-I, PD-1 mAb, or ATT-I+PD-1 mAb, to further assess the CD8+T-cell functions under each conditions. In the t-SNE plot analysis of the scRNA-seq data, types of cells in the tumors were assessed by their gene expression signatures. We determined the expression levels of T-cell activation (Icos, Cd28, Cd8a) and cytotoxicity (Ifng, Prf1, Pdcd1, and Sla2) genes in the tumors with each treatment (FIG. 6A). Our data confirms the enhanced activation and cytotoxicity of the combination treatment of ATT-I and PD1 mAb (FIG. 6B). Cytotoxicity levels in the combination treatment group displayed a significant increase in highly cytotoxic CD8+ T cells.

Next, we applied patient-derived tumor organoid (PDO) models to determine whether treatment of tumor organoids with ATT-I affects the cytotoxicity of autoglogous CD8+ T cells from the same tumor tissue. Freshly resected tumor tissues were obtained from two patients with colon adenocarcinoma. After tumor dissociation, tumor cells were then mixed with adherent stromal cells (fibroblasts, endothelial cells, and macrophages) to form PDOs. When the organoids reached 100 μm in diameter, they were co-cultured with the preactivated autologous CD8+T cells isolated from the same tumor tissue. Spheroids dissociation and T cell cytotoxicity were assessed (FIGS. 7A-7G). As expected, the ATT-I-treated PDOs became more vulnerable to CD8+ T cell killing as compared to the control PDOs, indicated by markedly high levels of organoid dissociation and tumor cell death. Collectively, the results of the in vivo and ex vivo studies suggest that ATT-I treatment further empower immune checkpoint blockade therapy in treating colorectal cancer by promoting T-cell infiltration and cytotoxicity.

What is claimed is:

1. A method of increasing the presentation of antigen-loaded MHC-I complex on a cancer cell, said method comprising contacting said cancer cell with ATT-I, wherein the cancer cell is a colorectal cancer (CRC) cell.

2. The method of claim 1 wherein the contact occurs in vivo.

* * * * *

SEQUENCE LISTING

```
<160> NUMBER OF SEQ ID NOS: 2

<210> SEQ ID NO 1
<211> LENGTH: 58
<212> TYPE: DNA
<213> ORGANISM: Artificial Sequence
<220> FEATURE:
<223> OTHER INFORMATION: Artificial construct

<400> SEQUENCE: 1

ccggttatag aacagggtca cattgctcga gcaatgtgac cctgttctat aatttttg       58


<210> SEQ ID NO 2
<211> LENGTH: 58
<212> TYPE: DNA
<213> ORGANISM: Artificial Sequence
<220> FEATURE:
<223> OTHER INFORMATION: Artificial construct

<400> SEQUENCE: 2

ccgggtgaat gttgacatca ttaatctcga gattaatgat gtcaacattc actttttg       58
```